US007351875B2

(12) United States Patent
Hogarth et al.

(10) Patent No.: US 7,351,875 B2
(45) Date of Patent: Apr. 1, 2008

(54) FCγRIIA TRANSGENIC ANIMAL MODEL FOR AUTOIMMUNE DISEASE

(75) Inventors: Phillip Mark Hogarth, Williamstown (AU); Patricia Lesley Mottram, St Kilda (AU); Caroline Tan Sardjono, West Java (ID)

(73) Assignee: Trillium Therapeutics, Inc. (CA)

( * ) Notice: Subject to any disclaimer, the term of this patent is extended or adjusted under 35 U.S.C. 154(b) by 69 days.

(21) Appl. No.: 10/517,251

(22) PCT Filed: Jun. 6, 2003

(86) PCT No.: PCT/AU03/00718

§ 371 (c)(1),
(2), (4) Date: Dec. 7, 2004

(87) PCT Pub. No.: WO03/104459

PCT Pub. Date: Dec. 18, 2003

(65) Prior Publication Data

US 2005/0177876 A1    Aug. 11, 2005

(30) Foreign Application Priority Data

Jun. 7, 2002   (AU) ..................... PS2856
Aug. 1, 2002   (AU) ..................... 2002950529

(51) Int. Cl.
G01N 33/00  (2006.01)
A01K 67/027 (2006.01)
C12N 15/00  (2006.01)

(52) U.S. Cl. .............................. 800/3; 800/18; 800/21; 800/25

(58) Field of Classification Search ............... 800/8, 800/3, 21, 18, 25
See application file for complete search history.

(56) References Cited

FOREIGN PATENT DOCUMENTS

| WO | PCT WO 95/28959 | 11/1995 |
| WO | PCT WO 96/08512 | 3/1996 |
| WO | 01/53312 | 7/2001 |
| WO | 03/101485 | 12/2003 |

OTHER PUBLICATIONS

See Wall et al. (2002) Theriogenology 57:189-201.*
Verma et al. (1997) Nature, vol. 389, p. 239.*
Pfeifer and Verma (2001) Annu. Rev. Genomics. Hum. Genet. 2:177-211.*
Johnson-Saliba et al. (2001) Curr. Drug. Targets 2:371-99.*
Shoji et al. (2004) Current Pharmaceutical Design 10 :785-796.*
Houdebine et al. (2000) Transgenic Research 9:305-320.*
Kolb et al. (1999) Gene 227:21-31.*
Sigmund, C., (2000) Arterioscler. Thromb. Vasc. Biol., p. 1425-1429.*
http://www.ucmp.berkeley.edu/mammal/rodentia/rodentia.html, pp. 1-2.*
"Functional Analysis of Human Fc-gamma-RII (CD32) Isoforms Expressed in B Lymphocytes", Van Den Herik-Oudijk, Ingrid E. et al., Journal of Immunology, vol. 152, No. 2, 1994, pp. 574-585.
"Phagosomal Maturation, Acidification, and Inhibition of Bacterial Growth in Nonphagocytic Cells Tranfected with FC-gamma-RIIA Receptors", Downey G. P. et al., Journal of Biological Chemistry, American Society of Biochemistry and Molecular Biology, Inc., Birmingham, U.S., vol. 274, No. 40, Oct. 1, 1999, pp. 28436-28444.
"Modulation of Immune Complex-Induced Inflammation in Vivo by the Coordinate Expression of Activation and Inhibitory FC Receptors", Clynes, R. et al., Journal of Experimental Medicine, Tokyo, Japan, vol. 189, No. 1, Jan. 4, 1999, pp. 179-185.
"The Role of Human Fc Receiptor FcγRIIA in the Immune Clearance of Platelets: A Transgenic Mouse Model", McKenzie et al., The Journal Immunology, pp. 4311-4318 (1999) vol. 162.
"Functional Consequences of the Interaction Between T-cell Antigen Receptors and FcγRs on T Cells", Kwack et al., Immunology Letters, 44 (1995) pp. 139-143, Elsevier Science B.V.

* cited by examiner

*Primary Examiner*—Anne M. Wehbe
(74) *Attorney, Agent, or Firm*—Sheridan Ross P.C.

(57) ABSTRACT

The present invention provides a FcγRIIa transgenic non-human animal model for autoimmune disease, particularly arthritis. This invention also provides a method of using this model to screen compounds that can reduce aberrant immune activity including aberrant immune complex formation aberrant immune complex clearance and immune complex induced inflammation. This invention also provides means of using this model to treat or prevent autoimmune disease.

8 Claims, 14 Drawing Sheets

Figure 5
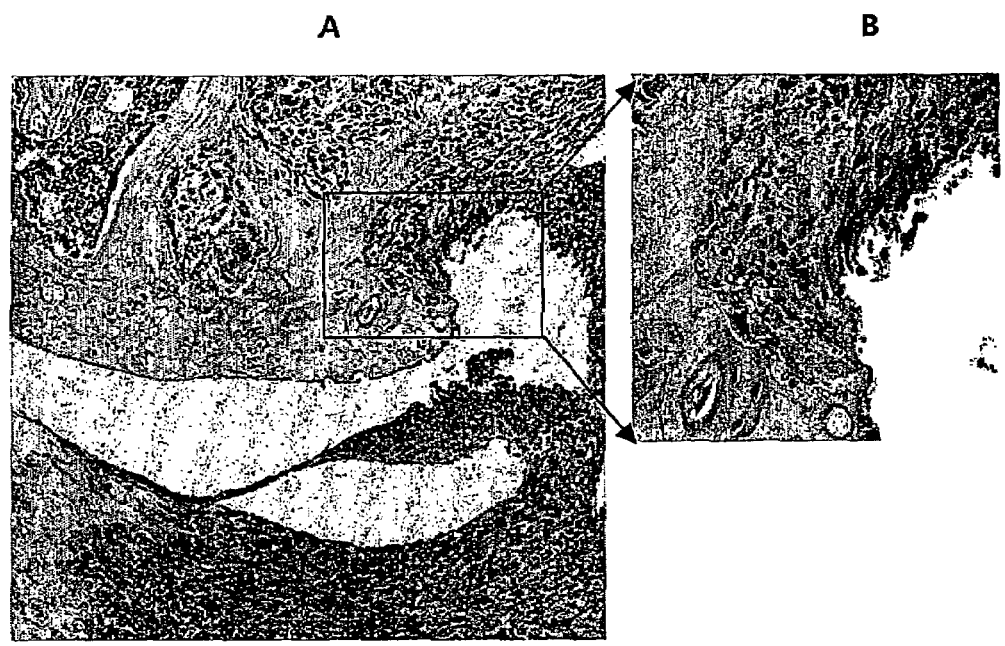
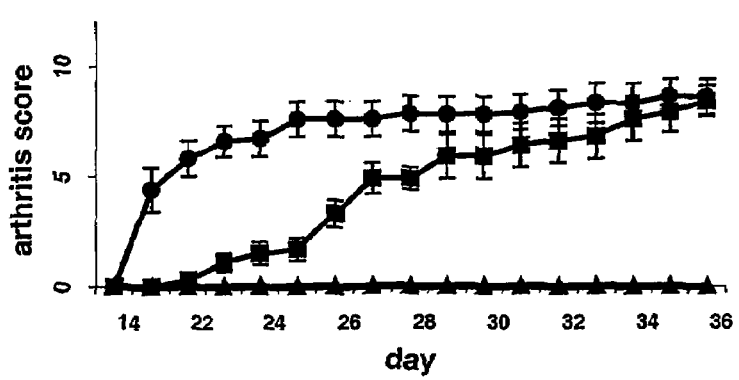
C

Figure 8A            Figure 8B

FCγRIIA TRANSGENIC ANIMAL MODEL FOR AUTOIMMUNE DISEASE

This application is a national stage application under 35 U.S.C. 371 of PCT Application No. PCT/AU03/00718, filed Jun. 6, 2003, which published in English and designated the United States. PCT/AU03/00718 claims priority under 35 U.S.C. §119(a)-(d) and 35 U.S.C. 365(b) from Australian Application No. 2002950529, filed Aug. 1, 2002 and from Australian Application No. PS 2856, filed Jun. 7, 2002. The entire disclosure of each of the above-identified applications is incorporated herein by reference.

FIELD OF THE INVENTION

The present invention relates to a non-human transgenic animal model for autoimmune disease, particularly arthritis. The invention also relates to methods for identifying compounds that can reduce aberrant immune activity and immune complex associated inflammation. This invention also relates to methods for identifying a mode of autoimmune disease development and for the identification of compounds that ameliorate this and the processes associated with this that lead to disease.

BACKGROUND OF THE INVENTION

Receptors for the Fc domain of IgG (FcγRs) amongst other factors are known to play a role in the regulation of the immune system. Currently, three classes of FcγRs are distinguished on cells of the immune system: the high-affinity receptor FcγRI (CD64), capable of binding monomeric IgG; the low-affinity receptors FcγRII (CD32) and FcγRIII (CD16), which interact preferentially with complexed IgG. Although these receptors show overlapping binding patterns for IgG subclasses, they vary in their cellular effector functions. FcγRI, FcγRIIa and FcγRIIIa are activating receptors, characterised by the presence of an immunoreceptor tyrosine-based activation motif immunoreceptor tyrosine-based activation motif (ITAM), either in the cytoplasmic domain of the receptor (FcγRIIa) or associated with the receptor as an accessory signalling subunit (γ and/or β chains associated with FcγRI and FcγRIIIa). By contrast, FcγRIIb is an inhibitory receptor, containing an immunoreceptor tyrosine-based inhibitory motif (ITIM) in its cytoplasmic domain. A marked exception to this dichotomy is FcγRIIIb; this receptor is linked to the outer leaflet of the plasma membrane by a glycosyl phosphatidylinositiol (GPI) anchor and does not contain or associate with ITAMs or ITIMs. There is presently no homolog described for FcγRIIa or FcγRIIIb in mice.

Whilst FcγR:Ig interactions are important effector systems in immunity, their role in autoimmune disease is uncertain. In humans the major inflammatory cells—macrophages, neutrophils, eosinophils and mast cells are known to express FcR receptors, including FcγRI, FcγRIIa, FcγRIIb, and FcγRIIIa, or FcγRIIIb.

FcγRIIa is present only in humans and higher primates, so there is no equivalent in mice or other rodents. The receptor is of particular interest because of the dependence of other Fc receptors on this receptor for their signal transduction and cell activating properties (Chuang et al. 2000). FcγRIIa can be expressed in transgenic mice with the same expression pattern as in humans (McKenzie et al. 1999). Thus human FcγRIIa can interact appropriately with intracellular signalling pathways in the mouse and appear normal in all respects, although changes in cross-species regulation in transgenics should always be considered in interpreting results. Transgenic mice expressing the human FcγRIIa have shown that this receptor is a major factor in platelet destruction in immune thrombocytopenia (McKenzie et al. 1999). The role of FcR receptors in inducing cell activation is known for in vitro systems, but their role in inflammation in vivo is less understood and has recently been studied, as described herein.

As a result of the use of gene knock out animals, the scientific and medical communities believe that the principal receptor involved in the induction of inflammation in vivo is FcγRIII (also known as CD16). Many studies in the literature indicate this and this has formed part of recent text book descriptions of immune complex induced inflammation. It was therefore very surprising that transgenic mice expressing the human FcγRIIa are highly sensitive to immune complex induced inflammation, also spontaneously develop inflammation in a variety of organs and tissues characteristic of a number of autoimmune diseases such as rheumatoid arthritis, systemic lupus erthemotosus (SLE), induced autoimmune disease such as glomerular basement membrane nephritis. Moreover, mice that develop these surprising inflammatory sensitivities are also useful for testing drugs.

However, no studies have examined the role of this FcR in autoimmune disease, such as SLE, arthritis or any other immune complex disorders, for example, the role of this Fc receptor in immune complex or antibody induced inflammation associated with autoimmune diseases. Inflammation in these diseases can include vasculitis, lupus nephritis and arthritis. Inflammation can also occur in diseases not necessarily classified as autoimmune such as infectious arthritis, in renal diseases such as mixed cryoglobulinemia, bacterial infections, in malignant diseases, in gastrointestinal diseases, complement deficiencies and in a number of miscellaneous conditions.

Accordingly, there remains a need for providing effective methods and models for autoimmune disease and methods for identifying compounds that can reduce aberrant immune activity, inflammation and disease processes. The surprising observation of the increased sensitivity to collagen induced arthritis in the transgenic mice whose genetic make up is composed of genes from otherwise genetically resistant mice, together with the observation of a spontaneous autoimmune disease, including arthritis was surprising. More surprising was that on further analysis of the transgenic animals, evidence of spontaneous autoimmunity and inflammation in tissues was evident. Inflammation in kidneys and in lungs occurred in many, though not all mice and histological examination of the joints showed features characteristic of rheumatoid arthritis, i.e. bone destruction and panus formation or features more characteristic of arthritis associated with diseases such as SLE where panus does not form. It would appear therefore that the presence of human FcγRIIa receptor in these mice allows the development of quite different inflammatory processes in different tissues that make up different clinical diagnoses.

SUMMARY OF THE INVENTION

A first aspect of the present invention is a method for screening a compound that is able to suppress aberrant immune activity, the method comprising the steps of:

(a) administering a compound to be screened to a non-human transgenic animal that has been modified to express human FcγRIIa receptor such that the transgenic animal is susceptible to an autoimmune disease; and (b) assessing the transgenic animal to determine if the compound reduces aberrant immune activity in the animal.

Preferably, the compound can reduce aberrant immune activity, such as but not limited to, aberrant immune complex formation, aberrant immune complex clearance or immune complex induced inflammation in a subject. The method of the present invention preferably includes the additional step of (c) assessing the transgenic animal to determine if the compound reduces immune complex induced inflammation.

A preferred aspect of the present invention is a method for screening a compound that is able to suppress an autoimmune disease, the method comprising the steps of:

(a) administering a compound to be screened to a non-human transgenic animal that has been modified to express human FcγRIIa receptor such that the transgenic animal is susceptible to an autoimmune disease; and (b) assessing the transgenic animal to determine if the compound reduces aberrant immune activity in the animal.

The non-human transgenic animal is preferably resistant to collagen-induced arthritis prior to being modified to express the human FcγRIIa receptor. Preferably, the transgenic animal is a transgenic mouse derived from the strains C57BL/6 and SJL that has been modified to express human FcγRIIa receptor. The aberrant immune activity preferably includes aberrant immune complex formation, aberrant immune complex clearance or immune complex induced inflammation. Preferably, the compound is able to reduce aberrant immune activity in the animal by inhibiting the activity of FcγRIIa expressed in the animal. In step (b) of the method, the aberrant immune activity can be preferably assessed in terms of clinical symptoms and/or pathological features of an autoimmune disease, such as arthritis or systemic lupus erthematosus (SLE). Preferably, the autoimmune disease is an autoimmune disease other than thrombocytopenia. Preferably, the autoimmune disease may include systemic lupus erthematosus (SLE), Crohn's disease, mixed cryoglubulinemia and other conditions involving pathology due to immune complexes. More preferably, the autoimmune disease is rheumatoid arthritis (RA) or more preferably collagen-induced arthritis (CIA). The assessment step (b) may include suitable assays for assessing aberrant immune activity, such as a suitable antibody assay. Other assays include analysis of cytokine expression by immunohistochemistry, PCR or ELISA in situ or in circulation, immune function tests such as antigen presentation, biochemical tests such as cell signalling.

Another aspect of the present invention is a method for screening a compound that is able to suppress an autoimmune disease, the method comprising the steps of:

(a) administering a compound to be screened to a non-human cell expressing human FcγRIIa receptor, wherein the cell is derived from a non-human transgenic animal that has been modified to express human FcγRIIa receptor such that the transgenic animal is susceptible to an autoimmune disease; and (b) assessing the cell to determine if the compound reduces aberrant immune activity in the cell.

The non-human transgenic animal is preferably resistant to collagen-induced arthritis prior to being modified to express the human FcγRIIa receptor. Preferably, the transgenic animal is a transgenic mouse derived from the strains C57BL/6 and SJL that has been modified to express human FcγRIIa receptor. Preferably, the aberrant immune activity includes aberrant immune complex formation, aberrant immune complex clearance or immune complex induced inflammation. The compound is preferably able to reduce aberrant immune activity in the cell by inhibiting the activity of FcγRIIa expressed in the cell. The assessment step (b) may include suitable assays for assessing aberrant immune activity, such as suitable antibody assays. Other suitable assays include analysis of cytokine expression by immunohistochemistry chemistry, PCR or ELISA in situ or in circulation, immune function tests such as antigen presentation, biochemical tests such as cell signalling.

A further aspect of the present invention is a compound when identified by the screening methods of the present invention that can reduce aberrant immune activity in a cell or animal.

The invention also provides a method of treating or preventing an autoimmune disease in a subject, the method comprising administering an effective amount of a compound that can reduce aberrant immune activity in the subject.

Preferably, the compound can reduce aberrant immune complex formation, aberrant immune complex clearance or immune complex induced inflammation in a subject. Preferably, the compound is able to reduce aberrant immune activity in the cell by inhibiting the activity of FcγRIIa expressed in the subject. The compound used in the method is preferably identified by the screening methods of the present invention. Preferably, the autoimmune disease is caused by aberrant immune complex formation, aberrant immune complex clearance or immune complex induced inflammation. The autoimmune disease is preferably arthritis or systemic lupus erythematosus (SLE). Preferably, the autoimmune disease is rheumatoid arthritis (RA) or more preferably collagen-induced arthritis (CIA).

The present invention also provides a composition for treating or preventing an autoimmune disease, the composition comprising an effective amount of a compound that can reduce aberrant immune activity in an animal, and a pharmaceutically acceptable diluent, excipient or carrier.

Preferably, the compound in the composition is identified by the screening methods of the present invention. The autoimmune disease is preferably arthritis or systemic lupus erythematosus (SLE). Preferably, the autoimmune disease is rheumatoid arthritis (RA) or more preferably collagen-induced arthritis (CIA).

Another aspect of the present invention is a non-human transgenic animal that has been modified to express human FcγRIIa receptor such that the transgenic animal is susceptible to an autoimmune disease, wherein the transgenic animal is resistant to collagen-induced arthritis prior to being modified to express the human FcγRIIa receptor.

The transgenic animal is preferably a mammal, such as, but not limited to, a rodent, dog, cat, pig, rabbit or non-human primate. More preferably, the transgenic animal is a mouse. More preferably, the transgenic animal is a transgenic mouse derived from the strains C57BL/6 and SJL that has been modified to express human FcγRIIa receptor. Preferably, the autoimmune disease is caused by aberrant immune complex formation, aberrant immune complex clearance or immune complex induced inflammation. The autoimmune disease is preferably arthritis or systemic lupus erythematosus (SLE). Preferably, the autoimmune disease is rheumatoid arthritis (RA) or more preferably collagen-induced arthritis (CIA).

In a preferred aspect of the invention the non-human transgenic animal as hereinbefore described is used in a method to identify a molecule associated with FcγRIIa ligand binding or a molecule dependent on FcγRIIa ligand binding. Preferably, the non-human transgenic animal is used in a method to identify a molecule including, but not limited to, antagonists or agonists of a ligand of FcγRIIa.

The present invention further provides a method of producing a non-human transgenic animal model for autoimmune disease, the method comprising the steps of:

(a) introducing a nucleic acid molecule encoding human FcγRIIa receptor to a cell of a non-human embryo;

(b) transferring the embryo to a foster mother; and (c) assessing the resultant born animal for susceptibility to autoimmune disease;

wherein the non-human transgenic embryo is resistant to collagen-induced arthritis prior to the introduction of a nucleic acid molecule encoding a human FcγRIIa receptor.

The transgenic animal is preferably a mouse. More preferably, the transgenic animal is a transgenic mouse derived from the strains C57BL/6 and SJL that has been modified to express human FcγRIIa receptor. Preferably, the autoimmune disease is caused by aberrant immune complex formation, immune complex clearance or immune complex induced inflammation. The autoimmune disease is preferably arthritis or systemic lupus erythematosus (SLE). Preferably, the autoimmune disease is rheumatoid arthritis (RA) or more preferably collagen-induced arthritis (CIA).

The invention also provides a method for producing a composition for treating or preventing an autoimmune disease, the method comprising (a) selecting the compound by the method as hereinbefore described; and (b) formulating the compound with a pharmaceutically acceptable diluent excipient or carrier to produce the composition.

BRIEF DESCRIPTION OF THE ACCOMPANYING FIGURES

FIG. 1A shows feet of a mouse with typical spontaneous arthritis at >30 weeks. Features include swelling, redness and rigidity of the joints, compared with feet of a normal mouse as shown in FIG. 1(B).

FIG. 2 shows a mouse hind limb with spontaneous arthritis (2A) and a normal mouse hind limb (2D). Histological staining (H&E sections, 400× magnification) of the knee joints of the arthritic mouse are shown in 2B and 2C, compared with a normal knee joint from an aged matched non-transgenic mouse (2E), showing inflammation with synovium hyperplasia and infiltrated by cells in the arthritic joint (2B). In mice with spontaneous arthritis, pannus formation and cartilage destruction were seen (in 29% of mice at 20-40 weeks and 33% of mice at >40 weeks), with inflammatory infiltration of the cartilage (2B). Interestingly in the other mice with the spontaneous arthritis, histology showed synovitis with fewer inflammatory cells and no pannus formation more characteristic of arthritis associated with disease such as Systemic Lupus Erythematosus (FIG. 2C). FIG. 2F shows the % cumulative incidence of spontaneous arthritis at 20 and 40 weeks.

FIG. 3 shows that eexamination of the organs from >20 week old transgenic mice revealed symptoms of autoimmune disease, with some of the features commonly seen in rheumatoid arthritis or human Systemic Lupus Erythematosus (SLE) (Edworthy 2001). The abnormalities included: pneumonitis with perivascular inflammation (FIG. 3A compared with normal lungs 3B) in 60-100% of mice (FIG. 3C) and glomerulopathy (FIG. 3D compared with a normal kidney, 3E) in 40-67% of older mice (FIG. 3F).

FIG. 4A-F show electron microscopy. FIG. 4A shows electron microscopy of the kidneys from an old transgenic mouse, at the junction of the uriniferous space (us) and a capillary (cap), revealing irregular floccular electron density intra basement membrane, representative of immune complex for deposition and identical to that seen in human kidneys from end-stage SLE patients (FIG.4B). Intra-glomerular immunocomplex deposition in the kidney of a mouse with glomerulopathy was also detected by a fluorescein-conjugated anti-mouse IgG (FIG.4C). This was a feature not seen in aged matched non-transgenic mice (FIG. 4D). High titres of anti-nuclear antibody were detected in the sera from 83% of transgenic mice aged >20 weeks, staining the cell nucleus with the "homogeneous nuclear pattern." (FIG. 4E). The same pattern was observed with an anti-histone antibody (huPIA3) (FIG. 4F), indicating that at least one component of the anti-nuclear antibody detected in the transgenic mice was anti-histone. Anti-nuclear antibodies (ANA) with this staining pattern are found in 70-95% of SLE patient and are one of the indicators for SLE (Edworthy 2001). Unlike the other features of autoimmune disease, ANA was also detected at low levels in transgenic mice examined at 12 weeks, and in age matched non-transgenic controls. This parallels the human situation, where up to 30% of the population may have serum ANA with no symptoms of autoimmune disease. No antibodies for double stranded DNA were seen (data not shown). No lung or kidney disease was seen in age matched non-transgenic C57BL/6 or (C57BL/6 ×SJL)$F_1$ mice.

FIG. 5 shows that DBA/1 mice (H-$2^q$) immunised with collagen type 11 (CII) develops an arthritis. Collagen induced arthritis (CIA) disease development and severity in FcγRIIa transgenic mice (C5BL/6 and SJL genetic background) was compared with the CIA-resistant background strains (C57BL/6 (H-$2^b$) and C57BL/6×SJL F1 (H-$2^{b/s}$)) with the susceptible DBA/1 (H-$2^q$) mice. The FcγRIIa transgenic mice developed arthritis with more rapid onset (as early as day 20) and greater severity than in the susceptible DBA/1 mice. The non-susceptible strains did not develop arthritis. FIG. 5C: circles show CIA score in transgenic mice: squares show the score in DBA/1 mice, triangles show C57BL/6 mice. Histology of the joints from FcγRIIa, DBA/1, C57BL/6 and (C57BL/6×SJL) $F_1$ mice culled on day 36 post arthritis induction confirmed this diagnosis. FcγRIIa transgenic mice showed massive synovial inflammation (FIG. 5A) and some articular erosion, caused by invading inflammatory cells replacing normal articular cartilage, and the development of pannus in the joint (FIG. 5B). These lesions were also found in the DBA/1 mice, but not in the joints from non-susceptible strains such as C57BL/6. Pannus formation progressing to degradation of the extracellular matrix, is a common feature of joints in humans with rheumatoid arthritis.

FIG. 6 shows a graph indicating the incidence of spontantenous arthritis in FcγRIIa mice. The percentage % incidence at each time point is shown in grey and the cumulative prevalence % in mice (n=50) with disease is shown in black. Note that this is a much larger cohort of mice to those anlysed in FIG. 2.

FIG. 7 shows a graph of the level of arthritis index over time for CIA in mice (n=4) treated with only two doses of VIB 153 (7.5 mg/dose on days 21 and 27), no treatment (n=28) or mice (n=15) treated with 4 doses of VIB 153 (7.5mg/dose on days 21, 24, 27, 30). CIA was induced by intradermal injection of an emulsion formed by combining 2 mg/ml chicken collagen type II (Sigma, St Louis, Mo.) dissolved in 10 mM acetic acid in an equal volume of CFA.

100 μl of the emulsion was injected i.d. into the base of the tail. The same dose was prepared and administered proximal to the primary site 21 days later (Campbell et al. 1997).

FIG. 8 shows typical swelling, redness and rigidity of the ankle joints, in the feeto of a transgenic mouse with CIA (A), in contrast to the normal appearance of the feet of (B) a treated transgenic mouse (4 doses of VIB 153, 7.5 mg/dose on days 21, 24, 27, 30) at day 32.

DETAILED DESCRIPTION OF THE INVENTION

Figure 1A:
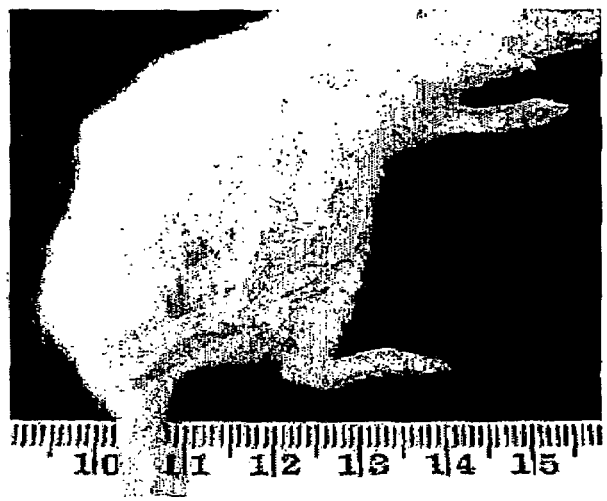

A first aspect of the present invention is a method for screening a compound that is able to suppress aberrant immune activity, the method comprising the steps of:

(a) administering a compound to be screened to a non-human transgenic animal that has been modified to express human FcγRIIa receptor such that the transgenic animal is susceptible to an autoimmune disease; and (b) assessing the transgenic animal to determine if the compound reduces aberrant immune activity in the animal.

Preferably, the compound can reduce aberrant immune activity, such as but not limited to, aberrant immune complex formation, aberrant immune complex clearance or immune complex induced inflammation in a subject. The method of the present invention preferably includes the additional step of:

(c) assessing the transgenic animal to determine if the compound reduces immune complex induced inflammation.

In a preferred aspect of the invention there is provided a method for screening a compound that is able to suppress an autoimmune disease, the method comprising the steps of:

(a) administering a compound to be screened to a non-human transgenic animal that has been modified to express human FcγRIIa receptor such that the transgenic animal is susceptible to an autoimmune disease; and (b) assessing the transgenic animal to determine if the compound reduces aberrant immune activity in the animal.

In the present specification the term "autoimmune disease" is to be understood to include a heterogeneous group of disorders in which the recognition of self antigens by lymphocytes is involved in pathogenic organ damage (for example see tables 22-1, 22-2 and 12-2 of Edworthy (2001). Antibodies and immune complexes can also be involved in tissue damage in disease not strictly autoimmune in nature. The term therefore includes diseases or conditions that are caused by aberrant immune activity. The phrase "aberrant immune activity" refers to abnormal immune function in a cell, such as but not limited to, aberrant antibody or immune complex formation, aberrant antibody or immune complex clearance or immune complex induced inflammation. Preferably, the aberrant immune activity includes elevated immune complex formation in a cell compared to normal cells. The aberrant immune activity may preferably include elevated levels of antibodies or immune complex clearance in a cell compared to normal cells. The autoimmune disease is preferably caused by aberrant immune complex formation. (see Edworthy, 2001).

Aberrant immune complex formation is typically characterised by the presence of soluble immune complexes, formation of complexes in situ, and the deposition of immune complexes in target organs. The autoimmune disease may be preferably caused by aberrant immune complex clearance. Aberrant immune complex clearance is typically characterised by the inability of phagocytes of the reticuloendothelial system to bind immune complexes via FcR. This can be due to abnormalities in or lack of phagocytic cells, aberrations of the FcR, or over-production of immune complexes due to uncontrolled anti-self antibody production.

The autoimmune disease is preferably arthritis or systemic lupus erythematosus (SLE). Preferably, the autoimmune disease is rheumatoid arthritis (RA) or more preferably collagen-induced arthritis (CIA). Other autoimmune diseases or inflammatory conditions associated with antibody or immune complex formation are listed in Table 12-2 of Edworthy (2001).

The non-human transgenic animal is preferably resistant to collagen-induced arthritis prior to being modified to express the human FcγRIIa receptor. Preferably, the transgenic animal is a transgenic mouse derived from the strains C57BL/6 and SJL that has been modified to express human FcγRIIa receptor. The aberrant immune activity preferably includes aberrant immune complex formation and/or aberrant immune complex clearance. Preferably, the compound is able to reduce aberrant immune activity in the animal by inhibiting the activity of FcγRIIa expressed in the animal.

In step (b) of the method, the aberrant immune activity can be preferably assessed in terms of clinical symptoms and/or pathological features of an autoimmune disease, such as but not limited to arthritis or systemic lupus erythematosus (SLE). Preferably, the autoimmune disease is an autoimmune disease other than thrombocytopenia. Preferably, the autoimmune disease may include systemic lupus erthematosus (SLE), Crohn's disease, mixed cryoglubulinemia and other conditions involving pathology due to immune complexes. More preferably, the autoimmune disease is rheumatoid arthritis (RA) and most preferably collagen-induced arthritis (CIA). Clinical symptoms of an autoimmune disease or aberrant immune activity can include pathological cellular or tissue indicators that are recognised to be associated with autoimmune disease. For instance, the severity of an autoimmune disease such as arthritis may be assessed by the level of inflammation or swelling of a joint of an animal. Tissue samples of an animal may be assessed for damage characteristic of autoimmune diseases, such as arthritis. For example, histological examination of tissue sections can be carried out to identify damage such as pannus formation, infiltration, cartilage and/or bone damage or erosion. Other indicators of inflammatory, or autoimmune disease, include leukocyte infiltration of target organs such as lungs, pancreas, salivary glands, lungs, bowel, skin, muscle, testes and eyes lesions. Intra glomerular immune complex deposition, associated with high titre anti-nuclear antibodies is detected by immunohistology and electron microscopy. Anti-nuclear antibodies, Rheumatoid factor and enzyme-specific antibodies (eg anti-insulin) can be detected in ELISA assays.

The assessment step (b) of the method of screening may include suitable assays for assessing aberrant immune activity, such as a suitable antibody assay. For instance, Systemic Lupus Erthematosus (SLE) is an autoimmune disease characterised by the development of antinuclear antibodies (ANA), especially against DNA. Therefore, antinuclear antibodies can be used to assay the level of ANAs in an animal to test for SLE. Other assays are listed in table 11-2 of Edworthy (2001). In an aspect of the present invention there is provided a method for screening a compound that is able to suppress an autoimmune disease, the method comprising the steps of:

(a) administering a compound to be screened to a non-human cell expressing human FcγRIIa receptor, wherein the cell is derived from a non-human transgenic animal that has been modified to express human FcγRIIa receptor such that the transgenic animal is susceptible to an autoimmune disease; and (b) assessing the cell to determine if the compound reduces aberrant immune activity in the cell.

The non-human transgenic animal is preferably resistant to collagen-induced arthritis prior to being modified to express the human FcγRIIa. Preferably, the transgenic animal is a transgenic mouse and more preferably of the C57BL/6 and genetic backgrounds that has been modified to express human FcγRIIa receptor. The mouse is characterised in the published paper by McKenzie et al. 1999, listed in references.

The aberrant immune activity preferably includes aberrant immune complex formation and/or aberrant immune complex clearance. The aberrant immune activity may be measured in a cell by preferably assessment in terms of clinical symptoms and/or pathological features of an autoimmune disease, such as arthritis or systemic lupus erythematosus (SLE). Preferably, the autoimmune disease is an autoimmune disease other than thrombocytopenia. Preferably, the autoimmune disease may include systemic lupus erthematosus (SLE), Crohn's disease, mixed cryoglubulinemia and other conditions involving pathology due to immune complexes. More preferably, the autoimmune disease is rheumatoid arthritis (RA) and most preferably collagen-induced arthritis (CIA). Clinical symptoms of an autoimmune disease or aberrant immune activity can include pathological cellular or tissue indicators that are recognised to be associated with autoimmune disease. For instance, the severity of an autoimmune disease such as arthritis may be assessed by the level of inflammation or swelling of a joint of an animal. Tissue samples of an animal may be assessed for damage characteristic of autoimmune diseases, such as arthritis. For example, histological examination of tissue sections can be carried out to identify damage such as pannus formation, infiltration, cartilage and/or bone damage or erosion. Other indicators of inflammatory autoimmune or connective tissue disease, include leukocyte infiltration of target organs such as lungs, pancreas, salivary glands, lungs, bowel, skin, muscle, testes and eye lesions. Intra glomerular immune complex deposition, associated with high titre anti-nuclear antibodies is detected by immunohistology and electron microscopy. Anti-nuclear antibodies, anti-collagen antibodies and Rheumatoid factor can be detected in by FACS and ELISA assays. Aberrant cytokine secretion (TNF-alpha, IL1, in RA) can be detected by ELISA, ELISPOT or RNAse protection assays. The assessment step (b) may include suitable assays for assessing aberrant immune activity, such as a suitable antibody assay. Anti-nuclear antibodies, anti-collagen antibodies and Rheumatoid factor can be detected in by FACS and ELISA assays.

The compound identified in the screening method of the present invention is preferably able to change aberrant immune activity in the cell by inhibiting the activity of FcγRIIa expressed in the cell. The compound may be an antagonist of FcγRIIa, such as an antibody against FcγRIIa or a soluble FcγRIIa protein fragment. Other suitable compounds that may be screened in the methods of the present invention may include naturally occurring compounds, such as but not limited to proteins and nucleic acid molecules, recombinant molecules or synthetic agents. The compound may be a Fc receptor modulating compound such as those described in U.S. Pat. No. 6,355,683 and WO 00/15214, the contents of which are herein incorporated. The compounds could also include antibodies, peptides, non natural peptides composed of non natural amino acids or non-natural bonds or synthesised using non natural synthetic methods or small chemical entities including inorganic and organic compounds or combinations thereof.

A further aspect of the present invention is a compound when identified by the screening methods of the present invention that can reduce aberrant immune activity in a cell or animal. Such compounds would be suitable as pharmaceutical agents in the treatment or prevention of autoimmune diseases. Moreover, the compounds identified by the methods of the present invention may be used in studies to further elucidate autoimmune disease.

The invention also provides a method of treating or preventing an autoimmune disease in a subject, the method comprising administering an effective amount of a compound that can reduce aberrant immune activity in the subject.

Preferably, the compound can reduce aberrant immune complex formation and/or aberrant immune complex clearance in a subject. Preferably, the compound is able to reduce aberrant immune activity in the cell by inhibiting the activity of FcγRIIa expressed in the subject. The compound used in the method is preferably identified by the screening methods of the present invention. Preferably, the autoimmune disease is caused by aberrant immune complex formation and/or aberrant immune complex clearance. The autoimmune disease is preferably arthritis or systemic lupus erythematosus (SLE). Preferably, the autoimmune disease is rheumatoid arthritis (RA) or more preferably collagen-induced arthritis (CIA).

In the method of the present invention, the term "effective amount" means a concentration of at least one compound sufficient to provide treatment or prevention of an autoimmune disease in a subject. The effective amount of a compound used in the methods of the present invention may vary depending on the subject and the type and level of autoimmune disease.

The subject treated by the methods of the invention may be selected from, but is not limited to, the group consisting of humans, sheep, cattle, horses, bovine, pigs, poultry, dogs and cats. The compound administered to a subject is preferably formulated as a pharmaceutical composition. The compound can be administered to humans and other animals orally, rectally, parentally (ie intravenously, intramuscularly, or sub-cutaneously), intracisternally, intravaginally, intraperitoneally, topically (as by powders, ointments, or drops), transdermally, bucally, or as an oral or nasal spray. Preferably, the compound is administered by injection to a tissue site of an autoimmune disease, such as a joint The injectable formulations can be sterilized, for example, by filtration through a bacterial-retaining filter, or by incorporating sterilizing agents in the form of sterile solid compositions which can be dissolved or dispersed in sterile water or other sterile injectable medium just prior to use. Solid dosage forms of the compounds for oral administration may include capsules, tablets, pills, powders, and granules. In such solid dosage forms, the active compound is mixed with at least one inert, pharmaceutically acceptable excipient or carrier such as sodium citrate or dicalcium phosphate and/or a) fillers or extenders such as starches, lactose, sucrose, glucose, mannitol, and silicic acid, b) binders such as, for example carboxymethylcellulose, alginates, gelatine, polyvinylpyrrolidone, sucrose, and acacia, c) humectants such as glycerol, d) disintegrating agents such as agar-agar, calcium carbonate, potato or tapioca starch, alginic acid, certain silicates, and sodium carbonate, e) solution retarding agents such as paraffin, f) absorption accelerators such as quaternary ammonium compounds g) vetting agents such as, for example, cetyl alcohol and glycerol monostearate, h) absorbents such as kaolin and bentonite day, and i) lubricants such as talc, calcium stearate, magnesium stearate, solid polyethylene glycols, sodium lauryl sulfate, and mixtures thereof. In the case of capsules, tablets and pills, the dosage form may also comprise buffering agents.

Accordingly, the present invention also provides a composition for treating or preventing an autoimmune disease, the composition comprising an effective amount of a compound that can reduce aberrant immune activity in an animal, and a pharmaceutically acceptable diluent, excipient or carrier.

Preferably, the compound in the composition is identified by the screening methods of the present invention. The autoimmune disease is preferably arthritis or systemic lupus erythematosus (SLE). Preferably, the autoimmune disease is rheumatoid arthritis (RA) or more preferably collagen-induced arthritis (CIA).

The compositions of the present invention may be formulated as solutions and emulsions. Suitable excipients, such as emulsifiers, surfactants, stabilisers, dyes, penetration enhancers and anti-oxidants may also be present in the compositions. Suitable carriers that may be added in the compositions can include, water, salt solutions, alcohols, polyethylene glycols, gelatine, lactose, magnesium stearate and silicic acid. The compositions may include sterile and non-sterile aqueous solutions. The compositions are preferably in a soluble form and the compounds are preferably, diluted in a soluble sterile buffered saline or water solution. The compositions can also be formulated as suspensions in aqueous, non-aqueous or mixed media. Aqueous suspensions may further contain substances that increase the viscosity of the suspension and may also contain stabilisers. The solutions may also contain buffers, diluents and other suitable additives. The compositions can include other adjunct components that are compatible with the activity of the compounds. The compositions of the present invention may be formulated and used as foams, including emulsions, microemulsions, creams and jellies. The formulations of the above compositions described would be known to those skilled in the field of pharmacy.

The compositions may be in the form of solid dosage forms, such as tablets, drags, capsules, pills, and granules which can be prepared with coatings and shells such as enteric coatings and other coatings well known in the pharmaceutical formulating art. They may optionally contain opacifying agents and can also be of a composition that they release the active ingredient(s) only, or preferentially, in a certain part of the intestinal tract, optionally, in a delayed manner. Examples of embedding compositions which can be used include polymeric substances and waxes.

If desired, and for more effective distribution, the compounds can be incorporated into slow release or targeted delivery systems such as polymer matrices, liposomes, and microspheres. The compounds can also be in microencapsulated form, if appropriate, with one or more of the above-mentioned excipients. Liquid dosage forms of the compounds for oral administration may include pharmaceutically acceptable emulsions, solutions, suspensions, syrups and elixirs. In addition to the compounds, the liquid dosage forms may contain inert diluents commonly used in the art such as, for example, water or other solvents, solubilizing agents and emulsifiers such as ethyl alcohol, isopropyl alcohol, ethyl carbonate, ethyl acetate, benzyl alcohol, benzyl benzoate, propylene glycol, 1,3butylene glycol, dimethyl formamide, oils (in particular, cottonseed, groundnut, corn, germ, olive, castor, and sesame oils), glycerol, tetrahydrofurfuryl alcohol, polyethylene glycols and fatty acid esters of sorbitan, and mixtures thereof.

Besides inert diluents, the compositions of the present invention can also include adjuvants such as wetting agents, emulsifying and suspending agents, sweetening, flavouring, and perfuming agents. The composition of the present invention may be in dosage forms for topical administration of the compound, such a powders, sprays, ointments and inhalants. The compound may be mixed under sterile conditions with a pharmaceutically acceptable carrier and any needed preservatives, buffers, or propellants which may be required to provide a pharmaceutical composition.

Another aspect of the present invention is a non-human transgenic animal that has been modified to express human FcγRIIa receptor such that the transgenic animal is susceptible to an autoimmune disease, wherein the transgenic animal is resistant to collagen-induced arthritis prior to being modified to express the human FcγRIIa receptor.

The transgenic animal is preferably a mouse. More preferably, the transgenic animal is a transgenic mouse derived from the strains C57BL/6 and SJL that has been modified to express human FcγRIIa receptor. Preferably, the autoimmune disease is caused by aberrant immune complex formation and/or aberrant immune complex clearance. The autoimmune disease is preferably arthritis or systemic lupus erythematosus (SLE). Preferably, the autoimmune disease is rheumatoid arthritis (RA) or more preferably collagen-induced arthritis (CIA).

The present invention further provides a method of producing a non-human transgenic animal model for autoimmune disease, the method comprising the steps of:

(a) introducing a nucleic acid molecule encoding human FcγRIIa receptor to a cell of a non-human embryo;

(b) transferring the embryo to a foster mother; and (c) assessing the resultant born animal for susceptibility to autoimmune disease;

wherein the non-human transgenic embryo is resistant to collagen-induced arthritis prior to the introduction of a nucleic acid molecule encoding a human FcγRIIa receptor.

The transgenic animal is preferably a mouse. More preferably, the transgenic animal is a transgenic mouse derived from the strains C57BL/6 and SJL that has been modified to express human FcγRIIa receptor. Preferably, the autoimmune disease is caused by aberrant immune complex formation and/or immune complex clearance. The autoimmune disease is preferably arthritis or systemic lupus erythematosus (SLE). Preferably, the autoimmune disease is rheumatoid arthritis (RA) or more preferably collagen-induced arthritis (CIA). The mouse is characterised in the published paper by McKenzie et al. 1999.

Throughout this specification the word "comprise", or variations such as "comprises" or "comprising", will be understood to imply the inclusion of a stated element, integer or step, or group of elements, integers or steps, but not the exclusion of any other element, integer or step, or group of elements, integers or steps.

The invention will hereinafter be described by way of the following non-limiting Figures and Examples.

EXAMPLE 1

Methods for Using a Transgenic Mouse Model for Autoimmune Disease (a) Transgenic Mice Expressing Human IgG Receptor FcγRIIa.

In transgenic mouse models of the present invention the following mice strains were used DBA/1 (H-$2^q$) males at 8-12 weeks old, C57BL/6 (H-$2^b$) and (C57BL/6×SJ (H-$2^{b/s}$) males or females at 8-15 weeks old, and transgenic mice expressing the FcγRIIa human transgene on platelets, neutrophils and macrophages at physiological levels, (as described in McKenzie et al. 1999). Transgenic males or females at 12-15 weeks old were used in collagen-induced arthritis (CIA) experiments, and >25 weeks old for the spontaneous autoimmune disease studies. All mice were bred and kept in clean conditions and were fed a standard diet and water ad libitum. The mouse is characterised in the published paper by McKenzie et al. 1999, listed in references.

(b) Collagen Type II Preparation.

Complete Freund's Adjuvant (CFA) was prepared by mixing 100 mg heat-killed *M tuberculosis* H37 Ra (Difco Laboratories, Detroit, Mich.) ground in 20 ml Incomplete Freund's Adjuvant (Difco Laboratories, Detroit, Mich.). An emulsion was formed by combining 2 mg/ml chicken collagen type II (Sigma, St Louis, Mo.) dissolved in 10 mM acetic add in an equal volume of CFA. 100 μl of the emulsion was injected i.d. into the base of the tail. The same dose was prepared and administered proximal to the primary site 21 days later (Campbell et al. 1997).

(c) Clinical Assessment of Arthritis.

Mice were examined 2-3 times per week from day 14 onwards. The severity of arthritis was rated on a scale from 0 to 3 for each extremity based on the swelling, redness, and the joint function. Score 0=normal, 1=mild swelling and/redness, 2=severe swelling and redness, 3=severe swelling and redness accompanied by joint dysfunction. The score of each mouse was calculated for the four limbs (maximum total score of 12 for each mouse) (Campbell et al. 1997).

(d) Assay for the Anti-Nuclear Antibodies (ANAs).

ANA tests were performed on Chinese Hamster Ovary (CHO) cells adhered to a Lab-Tek Chamber 8 well slide (Nunc, Naperville, Ill.) for 5 hours at 37° C. The cells then were fixed with 100% acetone for 5 min at room temperature, and washed 2 times with PBS/0.5% BSA. The cells were then incubated with mouse serum or anti-histone antibody raised in mice (antibody HuPIA3; cell line name 410.9D6A3 (Cosgrove 1987)) at various dilutions for 30 min on ice, followed by sheep anti-mouse IgG (Fab'2fragment)-FITC (Silenus, Melbourne, Australia) for 30 min on ice in the dark. For the staining shown in FIG. 4E serum was diluted 1:1000 and FIG. 4F anti-histone antibody in ascites was diluted 1:500.

(e) Histopathology Assessment.

At the end of experiments, the mice were culled and the organs were collected. Kidneys, lungs, and various other tissues were fixed with 10% formalin/PBS and embedded in paraffin. Sections (4-6 μm) were stained with hematoxylin and eosin. To detect immune complex deposition, kidney sections were stained with sheep anti-mouse IgG (Fab'2 fragment)-FITC (Silenus, Melbourne, Australia)

Joint tissues were decalcified before paraffin embedding with a solution containing 5% HCl, 3.5% acetic acid glacial, 95% ethanol, and 12.5% chloroform. Decalcification was considered complete when joints were bleached and flexible. Sections (4-6 μm) were stained with hematoxylin and eosin and examined for histological changes associated with arthritis (pannus formation, infiltration, cartilage and bone damage).

(f) Electron Microscopy Assessment

Samples of kidney were cut into 1-2 mm cubes using razor blades, and then fixed by immersion in fixative containing 2-8% paraformaldehyde, 2-5% glutaraldehyde in 0.15 M cacodylate buffer at pH 7.4. After fixation for a minimum of 6 hours at 4° C., tissues were rinsed in cacodylate buffer and post-fixed in 1% osmium tetroxide, in 0.15 M cacodylate buffer, pH 7.4 for 2 hours at room temperature. Samples were then washed in distilled water and dehydrated in 10% incremental concentrations of acetone prior to embedding in Procure-Araldite resin. During the dehydration procedure, tissues were stained en-block using a solution of 2% uranyl acetate in 70% acetone. Ultra thin sections were cut on a cryostat using glass knives and stained with 5% uranyl acetate in aqueous solution for 30 minutes at room temperature, followed by Reynolds lead citrate for 10 minutes. Ultra thin sections were examined in a Philips 300 electron microscope at 60 KV. * All reagents were from ProSciTech Australia.

(g) Antibody Detection.

Serum levels of total IgG and anti-collagen type II antibodies were assayed using ELISA using standard techniques. Briefly 96well Seroduster "U" vinyl plates (Costar, Cambridge, Mass.) were coated over night at 4° C. with 50 μl/well of 50 μg/ml collagen type II in 10 mM acetic acid. The plates were blocked with 2% BSA in PBS for 1 hour at room temperature. Mouse test sera were serial diluted and added to each well. The antibody bound to the plates was then detected by secondary sheep anti-mouse IgG (Fab'2fragment)-HRP (Amersham LIFESCIENCE, Buckinghamshire, England) and developed using ABTS (Boehringer Mannheim, Rockville, Md.). The absorbance at 405 nm was measured by an ELISA microreader.

(h) Statistical Analysis.

Data expressed as mean +/− SEM were compared using Student's test.

EXAMPLE 2

Results from a Spontaneous Arthritis (SA) Mouse Model

Figure 1B:

Spontaneous arthritis was observed in 47% of FcγRIIa transgenic mice at >20 weeks of age, increasing to 58% of mice aged >40 weeks and manifesting as swelling and reddening of the footpads and stiffening of the digits, knees and ankles (FIG. 1A, compared with aged matched control, FIG. 1B). Histological examination of the limbs confirmed the diagnosis of arthritis, shown in FIGS. 2B and 2C (compared with normal limbs from age matched non-transgenic mice (FIG. 2E)) revealed inflammation with synovium hyperplasia and infiltration by polymorphonuclear cells. In most of the cases with spontaneous arthritis, pannus formation and cartilage destruction were seen, with inflammatory infiltration of the cartilage (FIG. 2B). However, in about one third of mice with the spontaneous arthritis, histology showed sub acute synovitis, less inflammatory cells and no pannus formation (FIG. 2C). FIG. 2F shows the % cumulative incidence of spontaneous arthritis at 20 and 40 weeks, with pannus formation in 29% at 20 weeks and 33% at >40 weeks.

Examination of the organs from these and other >20 week old transgenic mice revealed symptoms of autoimmune connective tissue disease, with some of the features commonly seen in human Systemic Lupus Erythematosus (SLE) (Edworthy 2001). The abnormalities included pneumonitis with perivascular inflammation in 60-100% of mice (FIGS. 3A, 3C) and glomerulopathy in 40-67% (FIGS. 3D, F). Intra-glomerular immune complex deposition in the latter was detected by fluorescein-conjugated anti-mouse IgG (FIG. 4C); a feature not seen in aged matched non-transgenic mice (FIG. 4D). Electron microscopy of the kidneys from old transgenic mice (FIG. 4A) confirmed the immunohistochemistry, showing irregular floccular electron density intra basement membrane, representative of immune complex deposition and identical to that seen in human kidneys from end-stage SLE patients (FIG. 4B). Despite extensive kidney damage in older mice, increased proteinuria was not detected in these mice compared with non-transgenic older mice (data not shown). However, the onset of proteinuria in some autoimmune glomerulonephritis animal models apparently does not correlate with the sequale of glomerulonephritis and renal failure (Clynes, Dumitru et al. 1998). No lung or kidney disease was seen in age matched non-transgenic C57BL/6 or (C57BL/6×SJL)F$_1$ mice (FIGS. 3B and E) and none of the other organs examined (salivary gland, pancreas, gut, brain, heart, lymph nodes, spleen, skin eyes) showed abnormalities in either transgenic or non-transgenic mice.

Transgenic expression of activation-linked FcγRIIa clearly alters immune function in mice, making them susceptible to spontaneous immune complex disease. The observation of multiple symptoms of spontaneous immune complex disease in these mice provides the first direct evidence of a key role for this receptor in the development of such tissue specific autoimmune disease.

The present results show that spontaneous immune complex associated disease, manifesting initially as arthritis, was seen in mice carrying the human FcγRIIA gene. Non-transgenics on the same genetic background never developed disease at this age. These mice showed evidence of other immune complex mediated autoimmune reactivity, with high serum levels of anti-nuclear antibodies and immune complex deposition in the kidneys. Arthritis was characterised by inflammation of the synovium, with synovium hyperplasia, edema, cellular infiltration, and neovascularisation, leading to the formation of finger-like projections over the cartilage. This feature (pannus) is unique to rheumatoid arthritis and leads to chondrocyte breakdown, cartilage erosion and, eventually, bone reabsorption. Inflammation is stimulated by macrophage secretion of IL-1 and TNF alpha, leading to nitrous oxide and collagenase secretion, and chondrocyte death. T cell mediated induction of autoantibodies includes rheumatoid factor (RF), against the Fc portion of IgG. This is mostly IgM and seen in 70-90% of RA patients. Other autoantibodies, to collagen type II (the major cartilage component) and to keratin, are specifically diagnostic but not seen in all patients. FcγRIIa transgenic mice with spontaneous arthritis, show most of the above features at >25 weeks of age, providing evidence for the first time that expression of this FcR is involved in disease development.

EXAMPLE 3

Assessment of Systemic Lupus Erythematosus (SLE)

Systemic Lupus Erythematosus (SLE) is an autoimmune disease characterised by the development of antinuclear antibodies (ANA), especially against DNA. Antibodies to red and white blood cell surface antigens also develop, leading to anemia, thrombocytopenia, leukopenia, endothelial cell damage and vasculitis. Nerve damage is also seen. Renal failure and ultimately multiple organ failure are the end result. Many of these symptoms were seen in the aging FcγRIIa mice in that they also develop glomerulonephritis, pneumonitis and anti-nuclear antibodies. No mice were positive for rheumatoid factor. Detection of anti-nuclear antibodies which are symptoms of SLE were assessed in the following manner. High titres of anti-nuclear antibody were seen in 83% of the sera from transgenic mice aged >20 weeks, staining the cell nucleus with the "homogenous nuclear pattern". The same pattern was observed with an anti-histone antibody (huPIA3) (FIGS. 4E and 4F), indicating that the anti-nuclear antibody detected was anti-histone. Anti-nuclear antibodies with this staining pattern are found in 70-95% of SLE patients and are one of the indicators for SLE, although not diagnostic of the disease (Edworthy 2001). Unlike the other features of autoimmune disease, ANA was also detected in transgenic mice examined at 12 weeks, and in age matched non-transgenic controls. This parallels the human situation, where up to 30% of the population may have serum ANA with no symptoms of autoimmune disease. No antibodies for double stranded DNA, were seen (data not shown).

A summary of symptoms and disease incidence is shown in Table 1. As mentioned above, ANA appeared before other indicators of autoimmune disease, but was not clearly associated with disease development, since it was also seen in older non-transgenic animals. Of the 23 transgenic mice examined at >20 weeks, 19 (83%) had other symptoms of connective tissue disease. Of the disease free mice, 3 were aged 21-40 weeks and one was >40 weeks. Glomerulonephritis (Gn), with or without pneumonitis (Gn/Pn) was the most frequently observed disease: of 16 mice with these symptoms, 8 had Gn/Pn with no arthritis, 8 had arthritis and 5 of these had pannus. Gn severity increased with age but arthritis scores did not, with swelling and redness declining with time, although the joints remained stiff. Only one mouse (examined at 30 weeks) had all symptoms (ANA, Gn, arthritis, pannus). Three mice had arthritis only, and two of these showed pannus formation. Thus, these Gn/Pn and arthritis symptoms seem to develop independently. As expected, pannus development was dependent on arthritis (11 mice had arthritis: in 7 of these pannus was observed).

TABLE 1

| Disease and Symptoms* Summary | | | | | | | | |
|---|---|---|---|---|---|---|---|---|
| Normal mice C57Bl/6 (M) C57Bl/6xSJL (F1) | Sex | age culled (weeks) | ANA | dsDNA | Arthritis Score | Pannus | Kidney GN | Pneumonitis |
| M#1 |  | 25 | − | − | 0 | − | − | − |
| M#2 |  | 25 | + | − | 0 | − | − | − |
| M#old |  | >35 | + | − | 0 | − | − | − |
| M#1a |  | 32 | − | − | 0 | − | − | − |
| M#2b |  | 32 | + | − | 0 | − | − | − |
| F1#1 |  | >44 | − | − | 0 | − |  |  |
| F1#2 |  | >44 | − | − | 0 | − |  |  |
| F1#3 |  | >52 | + | − | 0 | − |  |  |
| Transgenic mice Group 1: <20 weeks | Sex | age culled (weeks) | ANA | dsDNA | Arthritis Score | Pannus | Kidney GN | Pneumonitis |
| S4.0.2 | M | 12 | − | − | 0 | − | − |  |
| S4.0.3 | M | 12 | + | − | 0 | − | − |  |
| S4.0.1 | M | 12 | + | − | 0 | − | − |  |
| S4.0.4 | M | 12 | + | − | 0 | − | − |  |
| Transgenic mice Group 2: 21-40 weeks | Sex | age culled (weeks) | ANA |  | Arthritis Score | Pannus | Kidney GN | Pneumonitis |
| S3.9N.13 | F | 25 |  |  | 0 | − | +++ | + |
| S3.5.17 | F | 32 | + |  | 0 | − | − |  |
| S3.1.1 | M | 35 | − |  | 0 | − | − |  |
| S3.1.2 | M | 36 | + |  | 0 | − | − |  |
| S3.4.14 | M | 37 | + |  | 0 | − | −/+ |  |
| S3.4.11 | M | 38 | + |  | 0 | − | + |  |
| S3.4.16 | M | 38 | − |  | 0 | − | −/+ |  |
| S3.7.4 | M | 36 |  |  | 3 | − | ++ |  |
| S3.1.5 | M | 36 | − |  | 6 | − | − |  |
| S2.1 |  | 30 | + |  | 10 | + | +++ |  |
| S8.0.3 | F | 31 |  |  | 10 | + | + | − |
| ITP6.3 |  | 25 | + |  | 11 | − | − | − |
| S8.0.2 | F | 32 | + |  | 12 | + | + | + |
| S8.0.1 | F | 40 | + |  | 12 | + | − | + |
| Transgenic mice GROUP 3: >40 weeks | Sex | age culled (weeks) | ANA |  | Arthritis Score | Pannus | Kidney GN | Pneumonitis |
| S3.2.8 | F | 52 |  |  | 0 | − | ++ |  |
| S3.6.76 | F | 52 | + |  | 0 | − | +++ | + |
| S7#2 | F | 54 | + |  | 0 | − | +++ |  |
| S3.2.6 | F | 52 | + |  | 0 | − | − |  |
| S3.2.5 | F | 52 |  |  | 0 | − | +++ |  |
| S7#1 | F | 47 | + |  | 4 | − | − |  |
| S7#3 | F | 54 | + |  | 5 | + | −/+ |  |
| S7#4 | F | 54 | + |  | 10 | + | ++ |  |
| S3.2.7 | F | 52 | + |  | 10 | + | − | + |

ANA, pannus and pneumonitis results are presented as positive (+) or negative (−).
Arthritis scores were calculated as described above (score from 0-12).
Kidney disease was scored as absent (−), mild (−/+), moderate (++), or severe (+++).

ANA appeared before other indicators of autoimmune disease, but was not clearly associated with disease development, since it was also seen in older non-transgenic animals. Of the 23 transgenic mice examined at >20 weeks, 19 (83%) had other symptoms of disease. Of the disease free mice, 3 were aged 21-40 weeks and one was >40 weeks. Glomrulonephritis (Gn), with or without pneumonitis (Gn/Pn) was the most frequently observed disease: of 16 mice with these symptoms, 8 had Gn/Pn with no arthritis, 8 had arthritis and 5 of these had pannus. Gn severity increased with age but arthritis scores did not with swelling and redness declining with time, although the joints remained stiff. Only one mouse (examined at 30 weeks) had all symptoms (ANA, Gn, arthritis, pannus). Three mice had arthritis only, and two of these showed pannus formation. Thus, these Gn/Pn and arthritis symptoms seem to develop independently. As expected, pannus development was dependent on arthritis (11 mice had arthritis—7 of these pannus was observed).

EXAMPLE 4

Results from a Collagen-Induced Arthritis (CIA) Mouse Model

CIA disease development and severity were compared in FcγRIIa transgenic mice with the CIA-resistant background strains (C57BL/6 H-$2^b$ and (C57BL/6×SJL)F1, H-$2^{b/s}$) and with the CIA susceptible DBA/1 (H-$2^q$) mice. In contrast to the background strains, that did not develop CIA, the FcγRIIa transgenic mice developed arthritis with more rapid onset (as early as day 20) and greater severity than in DBA/1 mice (FIG. 5C). Histology of the joints from FcγRIIa, DBA/1, C57BL/6 and (C57BL/6×SJL)F1 mice culled on day 36 post arthritis induction confirmed this diagnosis. FcγRIIa transgenic mice showed massive synovial inflammation (FIG. 5A) and some articular erosion, caused by invading inflammatory cells replacing normal articular cartilage, and the development of pannus in the joint (FIG. 5B). These lesions were also found in the DBA/1 mice, but not in the joints from non-susceptible strains such as C57BL/6. Pannus formation, due initially to the proliferation of fibroblast-like cells between articular surfaces, and progressing to degradation of the extracellular matrix, is a common feature of joints in humans with rheumatoid arthritis (Harris 2001). The results show that collagen-induced arthritis in FcγRIIa mice shows earlier onset and greater severity of disease than in DBA/1 mice.

EXAMPLE 5

Results of Anti-Collagen II Antibody and Rheumatoid Factor Detection

The titre of anti-collagen II antibody in the serum of transgenic, DBA/1 and C57BL/6 mice was measured by ELISA. Even though arthritis development was observed earlier in the FcγRIIa transgenic mice, they had lower antibody titres (detected at day 21 and day 36) than DBA/1 or C57BL/6 mice. These results suggest that inflammatory responses in the FcγRIIa transgenic mice are activated by low titre anti-collagen antibody, leading to rapid, early induction of arthritis. ELISA assays for antibodies to IgG, ie Rheumatoid factor (RF), gave no positive results. RF is normally not detected in mice with CIA.

EXAMPLE 6

Results from the Spontaneous Arthritis (SA) Model

Figure 6:
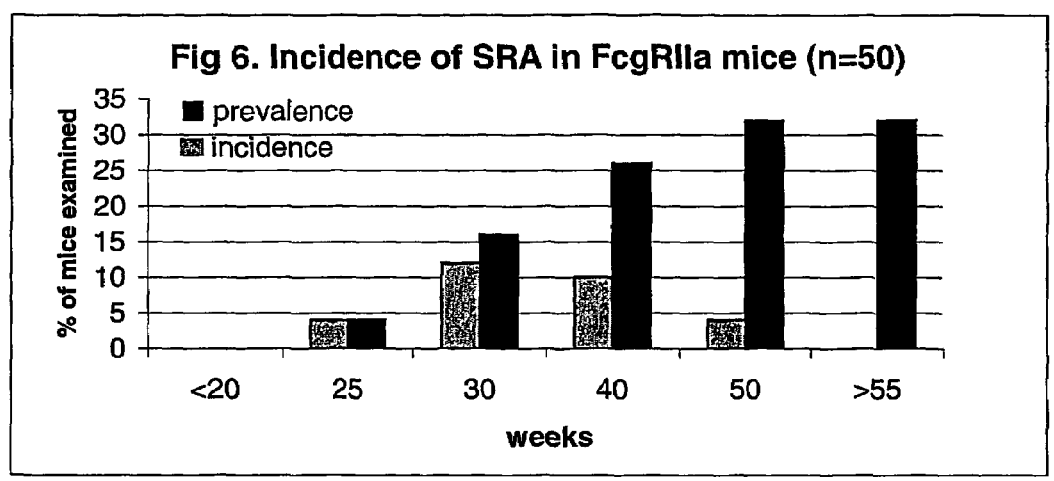

The transgenic mice used in this study expressed a uniquely human receptor for IgG, FcγRIIa, on the same cells and at physiological levels similar to that observed in humans. As they aged (>25 weeks) the mice developed spontaneous arthritis (SA), and showed abnormalities such as high titre anti-nuclear antibodies, inflammatory lung lesions and glomerulonephritis with intra-glomerular immune complex deposition. This study demonstrates a clear role for the human FcγRIIa in the development of immune complex disease in this mouse model system. FIG. 6 shows the % incidence of new disease at each time point (grey) and the cumulative prevalence % of mice (n=50) with disease (black).

The findings demonstrate that spontaneous arthritis is attributable to the expression of human FcγRIIa. As shown in FIG. 6, mice at 9-55 weeks of age were examined regularly for the development of arthritis.

Figure 2:
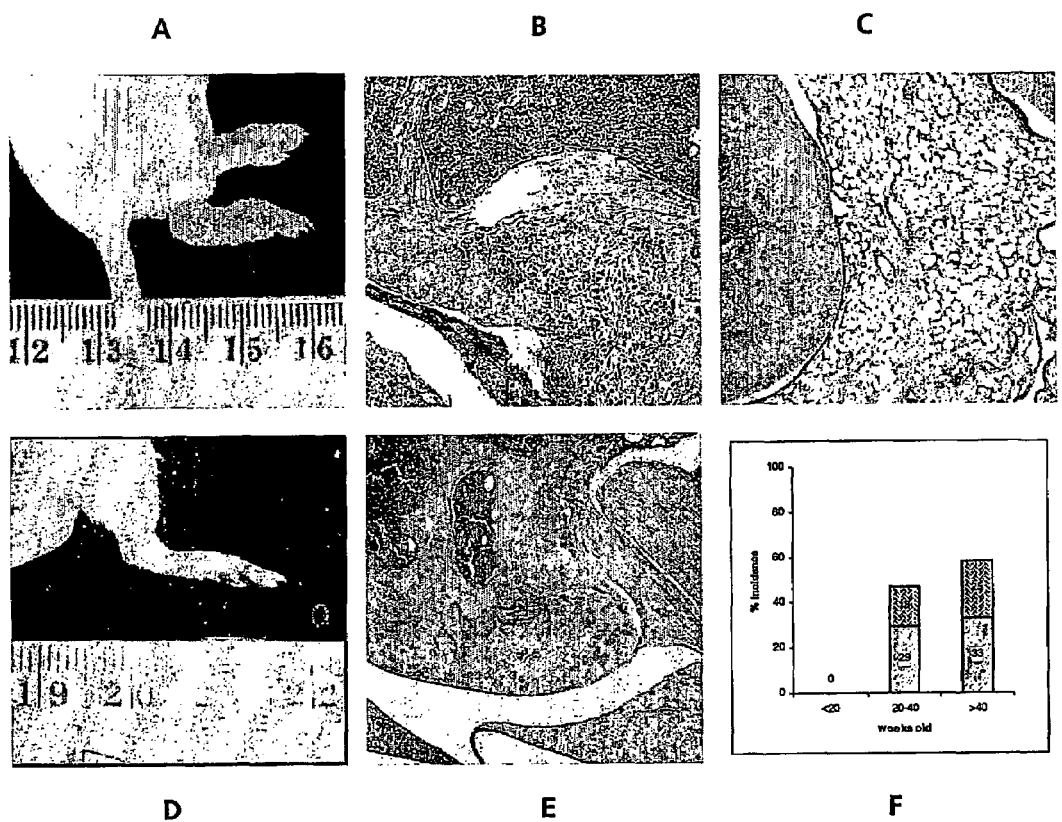

Histological examination was performed on tissue samples (kidneys, lungs, and various other tissues) collected at 9-55 weeks of age and fixed with 10% formalin/PBS and embedded in paraffin. Sections (4-6 μm) were stained with hematoxylin and eosin. To detect immune complex deposition, kidney sections were stained with sheep anti-mouse IgG (Fab'2 fragment)-FITC (Silenus, Melbourne, Australia). Joint tissues were decalcified before paraffin embedding with a solution containing 5% HCl, 3.5% acetic acid glacial, 95% ethanol, and 12.5% chloroform. Decalcification was considered complete when joints were bleached and flexible. Sections (4-6 μm) were stained with hematoxylin and eosin (H&E) and diseased joints showed the histological changes characteristic of arthritis (pannus formation, infiltration, cartilage and bone damage). FIG. 2 shows H&E stained sections of, (E): a normal knee joint and, (B): an arthritic knee joint from an SA mouse showing cartilage erosion and pannus formation.

EXAMPLE 7

Collagen-Induced Arthritis in a Transgenic Mouse Strain Expressing Human FcγRIIa In younger mice (8-12 weeks), the presence of the FcγRIIa gene in a mouse strain of mixed genetic background (C57BL/6/SJL, H-$2^{b/s}$) that is normally resistant to collagen-induced arthritis (CIA), conferred susceptibility to this disease. Furthermore, these mice showed earlier onset of CIA than DBA/1 (H-$2^q$) mice, a known susceptible strain (see below). CIA was induced in mice by i.d. injection of an emulsion of chicken collagen type II in Complete Freund's Adjuvant (CFA) into the base of the tail. Two injections were given, on day 0 and 21 of the experiment. The severity of arthritis was rated on a scale from 0 to 3 for each limb extremity based on swelling, redness, and the joint function.
Score 0=normal,
1=mild swelling and/redness of footpads or digits,
2=severe swelling and redness of footpads and digits,
3=severe swelling and redness accompanied by joint dysfunction.

The score for each mouse was calculated by adding the scores of the four limbs (maximum score of 12 for each mouse) (Campbell et al. 1997).

The findings show that expression of the FcγRIIa transgene in mice results in disease susceptibility in a previously resistant strain, with greater disease severity and earlier onset than mice with a susceptible background. Thus the addition of FcγRIIa not only converted the CIA non-susceptible mice background into a susceptible strain, but also induced autoimmune disease closely resembling human rheumatoid arthritis and/or SLE in older mice, a disease not previously reported in the founding mouse strains (C57BL/6 or SJL). The results demonstrate that FcγRIIa plays an important role in the autoimmune disease development, in particular Rheumatoid Arthritis and SLE. Strategies that result in the blocking or down regulating of this receptor will also provide a promising therapeutic approach to inhibit autoimmune disease, such as Rheumatoid Arthritis and SLE, in humans.

EXAMPLE 8

Testing of Compounds in Mice with Collagen-Induced Arthritis

Figure 7:
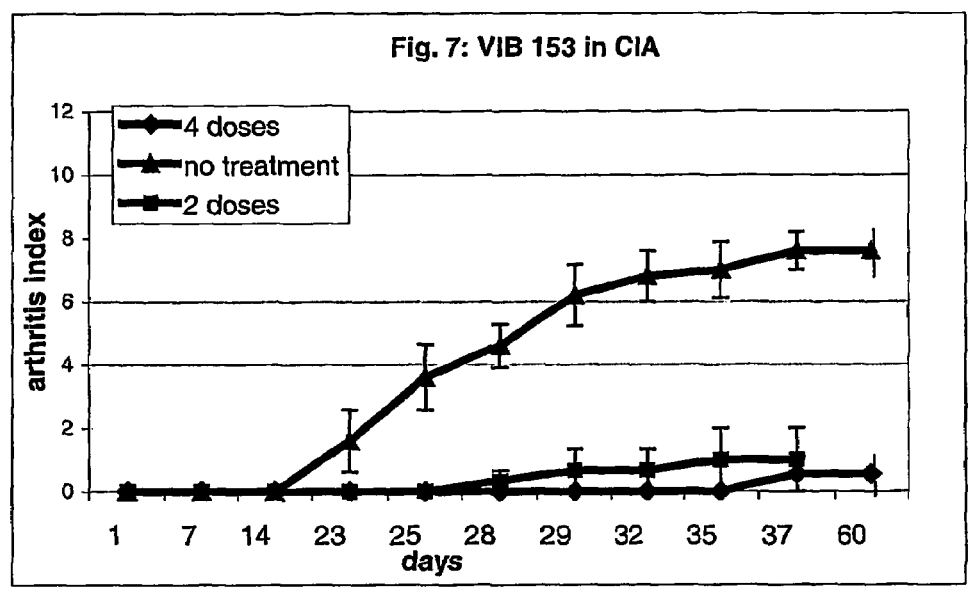

In control mice (n=28), over a period of 37 days disease progressed and resulted in a mean score of 7.5 (FIG. 7). No further increase in disease severity was seen from this time to >60 days. Mice (n=15) treated with four 7.5 mg doses of VIB 153 administered intra-peritoneally, commencing on day 21 (treated on day 21, 24, 27, 30), (FIG. 7) and examined until >60 days, showed no disease until day 37 and only one mouse developed mild disease during this time. Mice treated with only two doses of VIB 153 (7.5mg/dose on days 21 and 27) also showed very low levels of disease by day 37. Treated mice from the 4 dose group showed no signs of disease progression at >60 days. In the untreated mice, the swelling decreased over time, but the paws remained stiff and immobile at >60 days. Again, diseased joints showed the histological changes associated with arthritis (pannus formation, infiltration cartilage and bone damage), very similar to that seen with SA (see FIG. 5). FIG. 8 shows typical swelling and deformity in an untreated foot (A), in contrast to the normal appearance of the foot of a treated mouse (B) at day 32.

In a non-transgenic strain of mice that is susceptible to CIA (DBA/1) control mice (untreated) (n=27) were found to develop CIA over time, with a mean arthritis index of 7 at 37 days. Mice (n=12) treated with three 7.5mg doses of VIB 153 on days 21, 24 and 27 also developed CIA, and by day 37 the disease was of similar severity to that of the controls (see FIG. 9), showing that this drug has no effect when the transgene is absent.

EXAMPLE 9

Additional Testing of Compounds in a Collagen-Induced Arthritis Mouse Model

Mice with spontaneous arthritis at >30 weeks that were treated with three 7.5 mg doses of VIB 153 on days 0, 7, 14 after arthritis was observed had decreased swelling and redness at the end of treatment (mean scores reduced to 4, compared with 6 for untreated controls) but progression to joint stiffness was not prevented. Individual variation in this group of mice (n=3) was considerable, caused by the severity of disease at time of treatment Mice with higher scores were less amenable to treatment.

Figure 10:
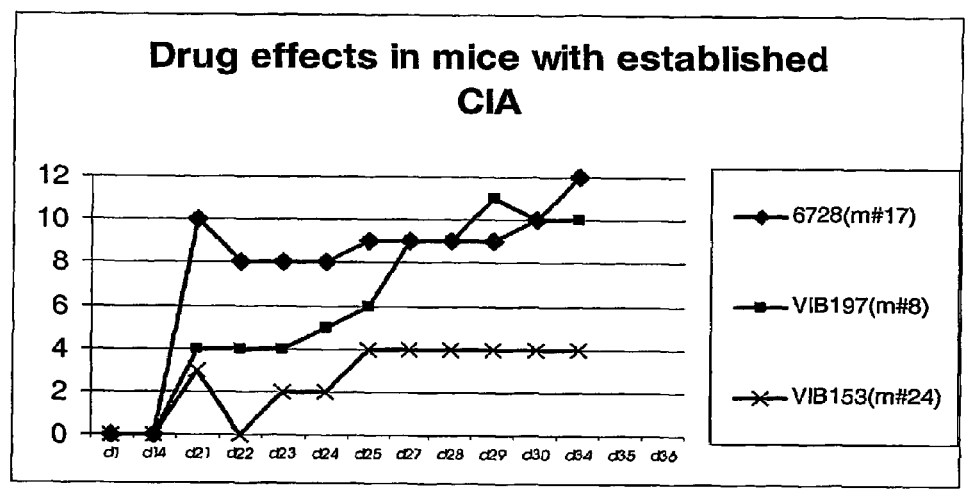
FIG. 10 and FIG. 11 show graphs of level of arthritis (index or score) for individual mice treated after arthritis was established (4 doses, 7.5mg/dose on days 21, 24, 27, 30) with the following drug compounds: 6727, 6728, VIB197 and VIB 153. This demonstrated that the drugs are effective in treating established arthritis when disease index is low.
Figure 11:
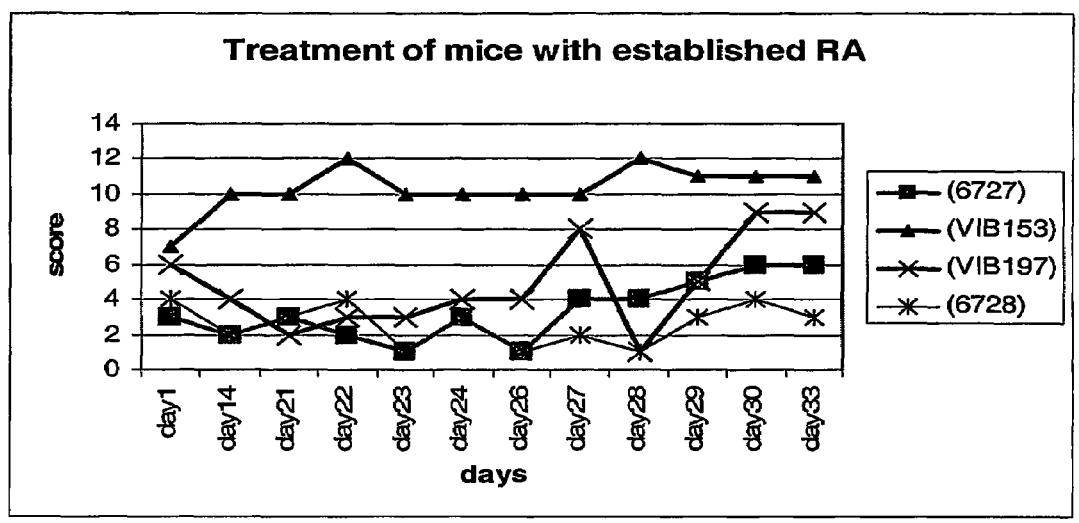

In mice with CIA, some developed disease prior to drug treatment (after the first collagen injection). These were treated with the same doses of drug as disease-free mice. Again, individual variation in this group of mice (n=2 mice/drug) was considerable, and depended on the severity of disease at time of treatment Mice with higher scores were less amenable to treatment (FIGS. 10 and 11).

CIA was induced in mice by i.d. injection of an emulsion of chicken collagen type II in Complete Freund's Adjuvant (CFA) into the base of the tail. Two injections were given, on day 0 and 21 of the experiment. The severity of arthritis was rated on a scale from 0 to 3 for each limb extremity based on swelling, redness, and the joint function.
Score 0=normal,
1=mild swelling and/redness of footpads or digits,
2=severe swelling and redness of footpads and digits,
3=severe swelling and redness accompanied by joint dysfunction.

The score for each mouse was calculated by adding the scores of the four limbs (maximum score of 12 for each mouse) (Campbell et al. 1997).

Figure 12:
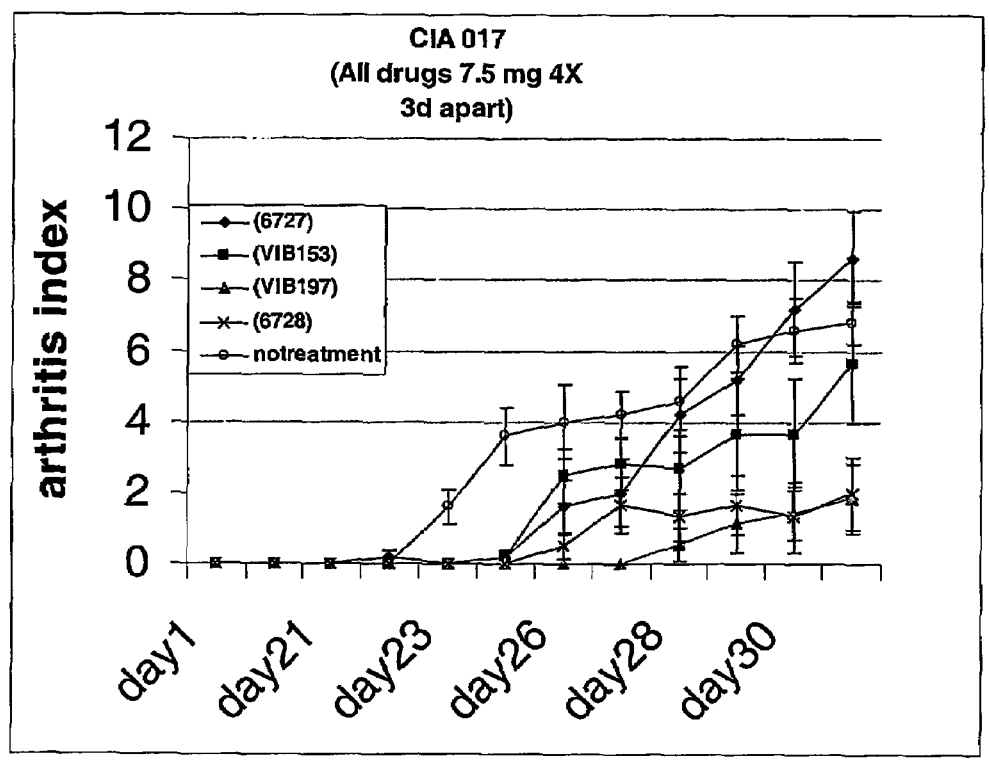
FIG. 12 and FIG. 13 show graphs of the level of arthritis (index or score) in mice with CIA treated with the following drug compounds prior to disease onset: 6727, 6728, VIB197, VIB 153 (4 doses, 7.5 mg/dose on days 21, 24, 27, 30) or no treatment (n=6 mice/group).
Figure 13:
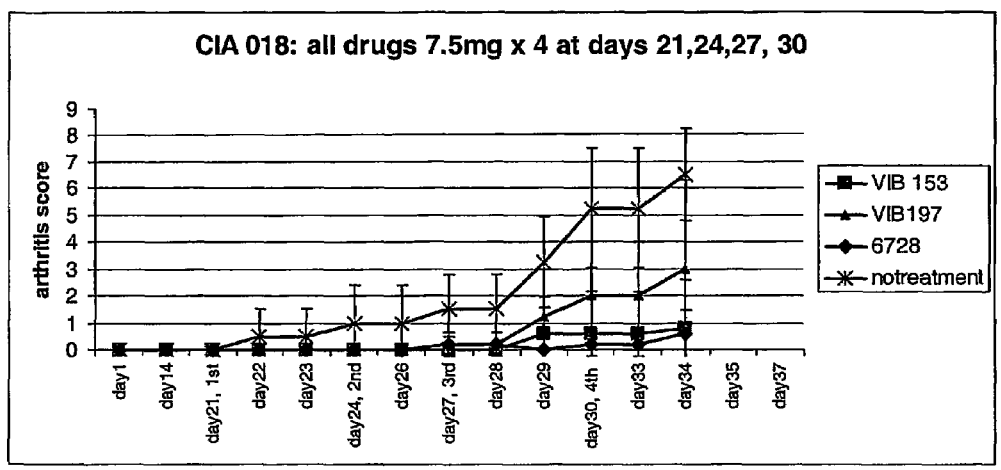

Mice were treated with four 7.5 mg doses of drug administered intra-peritoneally, commencing on day 21 (treated on day 21, 24, 27, 30), and examined until >60 days (see FIG. 12 and 13. In the untreated mice, the swelling decreased over time, but the paws remained stiff and immobile at >60 days. Again, diseased joints showed the histological changes associated with arthritis (pannus formation, infiltration, cartilage and bone damage), very similar to that seen with SA. All of the drugs tested (6727, 6728, VIB197, VIB 153) modified the development of CIA, either delaying the onset of disease or reduce severity significantly, with low scores maintained for >30 days.

It is clear from these studies that the presence of FcRIIa confers sensitivity to immune complexes on these mice despite there being all the other activating and inhibitory Fc receptors—FCRI and FcRIII as well as FcRIIb—present in these mice. It would therefore be expected that in diseases other than autoimmune diseases such sensitivity to antibodies and inflammation caused by antibodies and immune complexes would be evident in FcγRIIa transgenic mice and would be useful for testing compounds to potentially treat these diseases.

EXAMPLE 10

Treatment of CIA with Anti-T Cell or Anti-Inflammatory Agents

T cells are known to play a significant role in the induction of CIA. For instance, T cell inactivation with an anti-CD3 monoclonal antibody (KT3), that recognises the T cell receptor chain, before the onset of CIA in DBA/1 mice has been shown to reduce disease severity (Hughes, Wolos et al. 1994). In the present study anti-CD3 antibody was used at a dose that is known to be immunosuppressive in mice (Mottram, Murray-Segal et al. 2002), to treat FcγRIIa transgenic mice with induced CIA. CIA was induced in mice as described in Example 7, then the mice were treated on day 20, before disease onset and prior to the second collagen injection (day 21) and again on days 22, 23 and 25 with 0.5mg ip of anti-CD3. As reported for DBA/1 mice (Hughes, Wolos et al. 1994), this treatment delayed the onset of CIA, with the index remaining low in these mice until day 37 (FIG. 14).

Figure 14:
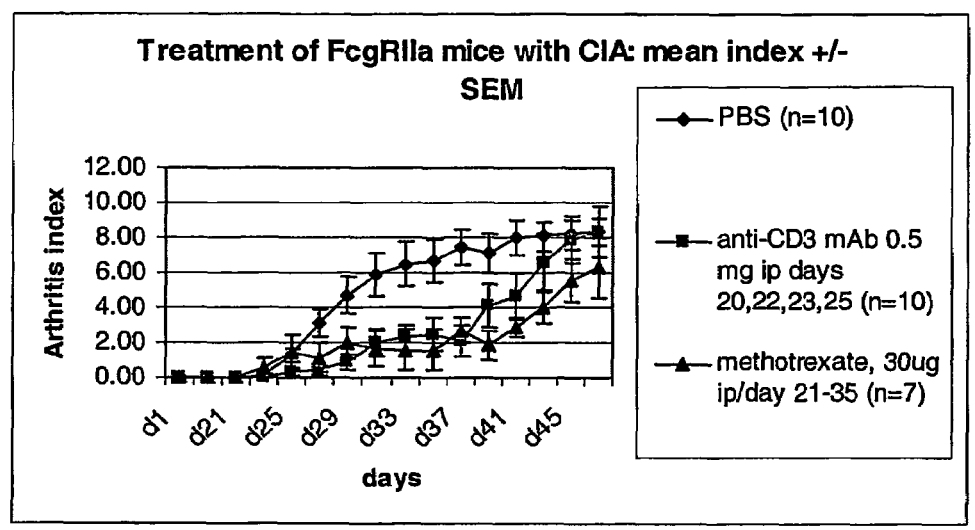
FIG. 14 shows a graph of the level of arthritis index in FcγRIIa transgenic mice with CIA treated prior to disease onset with known immunisuppressive and nati-inflammatory agents anti-CD3 monoclonal antibody or methotrexate compared with controls (PBS treated).

In the present study, treatment with methotrexate, a DMARD commonly used for the treatment of severe rheumatoid arthritis in humans (Hildner, Finotto et al. 1999), and known to be effective in delaying CIA in DBA/1- mice (Neurath, Hildner et al. 1999), was also effective in delaying CIA in the FcγRIIa transgenic mice (FIG. 14). Methotrexate was used at a low dose for 14 days from the time of the second collagen injection (1 mg/kg, ie 30 g/30 gm mouse from day 21-35) (FIG. 14). In both anti-CD3 and methotrexate treatment, arthritis was delayed due to depletion of inflammatory effector cells and disease increased in severity as immune function returned to normal after treatment ceased.

In contrast, treatment with anti-FcR agents (see above, examples 8 and 9) permanently halted disease progression, implying that essential initial steps in the inflammatory process were inhibited allowing disease prevention rather than delay. The data shown in FIG. 14 demonstrates that known treatments, including biological agents such as monoclonal antibodies and drugs such as methotrexate, effective for CIA in DBA/1 mice, are equally effective in the FcγRIIa transgenic mice. CIA in the DBA/1 mice has been used as a test model for anti-arthritis drugs for many years (Phadke, Fouts et al. 1985; Imaizumi, Hinoue et al. 1991). The data of the present study demonstrates that the FcγRIIa transgenic mice also respond to treatments that are effective in DBA/1 mice and these mice can therefore be used to test anti-arthritis drugs.

It will be appreciated by persons skilled in the art that numerous variations and/or modifications may be made to the invention as shown in the specific embodiments without departing from the spirit or scope of the invention as broadly described. The present embodiments are, therefore, to be considered in all respects as illustrative and not restrictive.

All publications discussed above are incorporated herein in their entirety. Any discussion of documents, acts, materials, devices, articles or the like which has been included in the present specification is solely for the purpose of providing a context for the present invention. It is not to be taken as an admission that any or all of these matters form part of the prior art base or were common general knowledge in the field relevant to the present invention as it existed in Australia or elsewhere before the priority date of each claim of this application.

REFERENCES:

Campbell, I. K., A. Bendele, et al. (1997). "Granulocyte-macrophage colony stimulating factor exacerbates collagen induced arthritis in mice." Ann Rheum Dis 56(6): 364-8.
Chuang, F., Saroli, M. and Unkeless, J. (2000). "Convergence of Fc gamma receptor IIA and Fc gamma receptor IIB signalling pathways in human neutrophils." J. Immunol. 164(1): 350-60.
Clynes, R., C. Dumitru, et al. (1998). "Uncoupling of immune complex formation and kidney damage in autoimmune glomerulonephritis." Science 279(5353): 10524.
Cosgrove, L. (1987). Monoclonal antibodies to platelet antigens. Department of Pathology. Melbourne, University of Melbourne.
Edworthy, S. (2001). Clinical manifestations of Systemic Lupus Erythematosus. Kelley's Textbook of Rheumatology. S. Ruddy, E. Harris and B. Sledge. Philadelphia, Pa., W. B. Saunders Company. 2:1105-1123.
Hildner, K., S. Finotto, et al. (1999). "Tumour necrosis factor (TNF) production by T cell receptor-primed T lymphocytes is a target for low dose methotrexate in rheumatoid arthritis." Clin Exp Immunol 118(1): 137-46.
Hughes, C., J. A. Wolos, et al. (1994). "Induction of T helper cell hyporesponsiveness in an experimental model of autoimmunity by using nonmitogenic anti-CD3 monoclonal antibody." J Immunol 153(7): 3319-25.
Imaizumi, K., H. Hinoue, et al. (1991). "Pathological evaluation of anti-rheumatic drugs on type II collagen-induced arthritis in DBA/1J mouse." Jikken Dobutsu 40(1): 95-9.
McKenzie, S. E., S. M. Taylor, et al. (1999). "The role of the human Fc receptor Fc gamma RIIA in the immune clearance of platelets: a transgenic mouse model."J Immunol 162(7): 4311-8.
Mottram, P. L., L. J. Murray-Segal, et al. (2002). "Remission and pancreas isograft survival in recent onset diabetic NOD mice after treatment with low-dose anti-CD3 monoclonal antibodies." Transpl Immunol 10(1): 63-72.
Neurath, M. F., K. Hildner, et al. (1999). "Methotrexate specifically modulates cytokine production by T cells and macrophages in murine collagen-induced arthritis (CIA): a mechanism for methotrexate-mediated immunosuppression." Clin Exp Immunol 115(1): 42-55.
Phadke, K., R. L. Fouts, et al. (1985). "Evaluation of the effects of various anti-arthritic drugs on type II collagen-induced mouse arthritis model."Immunopharmacology 10(1): 51-60.

The invention claimed is:

1. A method for screening a compound that is able to suppress aberrant immune activity, wherein the aberrant immune activity is selected from aberrant immune complex formation, aberrant immune complex clearance and immune complex induced inflammation, the method comprising the steps of:
   a. administering a compound to be screened to transgenic mouse generated by transgenically modifying an embryo from a strain, derived from strains C57BL/6 and SJL, that is resistant to collagen-induced arthritis, such that said mouse comprises and expresses a transgene for human FcγRIIa receptor, whereby the expression of said FcγRIIa renders the mouse susceptible to an autoimmune disease caused by aberrant immune complex formation, aberrant immune complex clearance or immune complex induced inflammation; and
   b. assessing the transgenic mouse to determine if the compound reduces aberrant immune activity in the mouse;
   wherein said autoimmune disease is selected from the group consisting of arthritis and systemic lupus erythematosus.

2. A method of screening a compound that is able to suppress an autoimmune disease caused by aberrant immune complex formation, aberrant immune complex clearance or immune complex induced inflammation by suppressing aberrant immune activity selected from aberrant immune complex formation, aberrant immune complex clearance and immune complex induced inflammation, the method comprising the steps of:
   a. administering a compound to be screened to a transgenic mouse generated by transgenically modifying an embryo from a strain, derived from strains C57BL/6 and SJL that is resistant to collagen-induced arthritis, such that said mouse comprises and expresses a transgene for human FcγRIIa receptor, whereby the expression of said FcγRIIa renders the mouse susceptible to an autoimmune disease caused by aberrant immune complex formation, aberrant immune complex clearance or immune complex induced inflammation; and
   b. assessing the transgenic mouse to determine if the compound reduces aberrant immune activity in the mouse;

wherein said autoimmune disease is selected from the group consisting of arthritis and systemic lupus erythematosus.

3. A method for screening a compound that is able to suppress an autoimmune disease caused by aberrant immune complex formation, aberrant immune complex clearance or immune complex induced inflammation, the method comprising the steps of:
   a. administering a compound to be screened to a non-human cell expressing human FcγRIIa receptor, wherein the cell is selected from the group consisting of platelets, neutrophils and macrophages, and wherein the cell is derived from a transgenic mouse generated by transgenically modifying an embryo from a strain, derived from strains C57BL/6 and SJL, that is resistant to collagen-induced arthritis, such that said mouse comprises and expresses a transgene for human FcγRIIa receptor, whereby the expression of said FcγRIIa renders the mouse susceptible to an autoimmune disease caused by aberrant immune complex formation, aberrant immune complex clearance or immune complex induced inflammation; and
   b. assessing the cell to determine if the compound reduces aberrant immune activity in the cell.

4. A method according to claim 1, wherein the method comprises assessing the transgenic mouse to determine if the compound reduces immune complex induced inflammation.

5. A method according to claim 1, wherein the compound reduces aberrant immune activity in the transgenic mouse by inhibiting the activity of FcγRIIa expressed in the rodent.

6. A method according to claim 1, wherein in step (b) the aberrant immune activity is assessed in terms of clinical symptoms and/or pathological features of an autoimmune disease.

7. A method according to claim 1, wherein the autoimmune disease is rheumatoid arthritis (RA).

8. A method according to claim 1, wherein the autoimmune disease is collagen-induced arthritis (CIA).

* * * * *

UNITED STATES PATENT AND TRADEMARK OFFICE
CERTIFICATE OF CORRECTION

| | | |
|---|---|---|
| PATENT NO. | : 7,351,875 B2 | Page 1 of 15 |
| APPLICATION NO. | : 10/517251 | |
| DATED | : April 1, 2008 | |
| INVENTOR(S) | : Hogarth et al. | |

It is certified that error appears in the above-identified patent and that said Letters Patent is hereby corrected as shown below:

The title page, should be deleted and substitute therefor the attached title page.

Delete Column 1 line 1 through Column 26 line 18 and substitute Column 1 line 1 through Column 26 line 11 as shown on the attached pages.

Signed and Sealed this

Sixteenth Day of November, 2010

David J. Kappos
*Director of the United States Patent and Trademark Office*

United States Patent
Hogarth et al.

(10) Patent No.: US 7,351,875 B2
(45) Date of Patent: Apr. 1, 2008

(54) FCγRIIA TRANSGENIC ANIMAL MODEL FOR AUTOIMMUNE DISEASE

(75) Inventors: Phillip Mark Hogarth, Williamstown (AU); Patricia Lesley Mottram, St Kilda (AU); Caroline Tan Sardjono, West Java (ID)

(73) Assignee: Trillium Therapeutics, Inc. (CA)

( * ) Notice: Subject to any disclaimer, the term of this patent is extended or adjusted under 35 U.S.C. 154(b) by 69 days.

(21) Appl. No.: 10/517,251

(22) PCT Filed: Jun. 6, 2003

(86) PCT No.: PCT/AU03/00718

§ 371 (c)(1),
(2), (4) Date: Dec. 7, 2004

(87) PCT Pub. No.: WO03/104459

PCT Pub. Date: Dec. 18, 2003

(65) Prior Publication Data

US 2005/0177876 A1    Aug. 11, 2005

(30) Foreign Application Priority Data

Jun. 7, 2002 (AU) .................................... PS2856
Aug. 1, 2002 (AU) ............................. 2002950529

(51) Int. Cl.
*G01N 33/00* (2006.01)
*A01K 67/027* (2006.01)
*C12N 15/00* (2006.01)

(52) U.S. Cl. ............................ 800/3; 800/18; 800/21; 800/25

(58) Field of Classification Search .................. 800/8, 800/3, 21, 18, 25
See application file for complete search history.

(56) References Cited

FOREIGN PATENT DOCUMENTS

| WO | PCT WO 95/28959 | 11/1995 |
|---|---|---|
| WO | PCT WO 96/08512 | 3/1996 |
| WO | 01/53312 | 7/2001 |
| WO | 03/101485 | 12/2003 |

OTHER PUBLICATIONS

See Wall et al. (2002) Theriogenology 57:189-201.*
Verma et al. (1997) Nature, vol. 389, p. 239.*
Pfeifer and Verma (2001) Annu. Rev. Genomics. Hum. Genet. 2:177-211.*
Johnson-Saliba et al. (2001) Curr. Drug. Targets 2:371-99.*
Shoji et al. (2004) Current Pharmaceutical Design 10 :785-796.*
Houdebine et al. (2000) Transgenic Research 9:305-320.*
Kolb et al. (1999) Gene 227:21-31.*
Sigmund, C., (2000) Arterioscler. Thromb. Vasc. Biol., p. 1425-1429.*
http://www.ucmp.berkeley.edu/mammal/rodentia/rodentia.html, pp. 1-2.*
"Functional Analysis of Human Fc-gamma-RII (CD32) Isoforms Expressed in B Lymphocytes", Van Den Henk-Oudijk, Ingrid E. et al., Journal of Immunology, vol. 152, No. 2, 1994, pp. 574-585.
"Phagosomal Maturation, Acidification, and Inhibition of Bacterial Growth in Nonphagocytic Cells Tranfected with FC-gamma-RIIA Receptors", Downey G. P. et al., Journal of Biological Chemistry, American Society of Biochemistry and Molecular Biology, Inc., Birmingham, U.S., vol. 274, No. 40, Oct. 1, 1999, pp. 28436-28444.
"Modulation of Immune Complex-Induced Inflammation in Vivo by the Coordinate Expression of Activation and Inhibitory FC Receptors", Clynes, R. et al., Journal of Experimental Medicine, Tokyo, Japan, vol. 189, No. 1, Jan. 4, 1999, pp. 179-185.
"The Role of Human Fc Receiptor FcγRIIA in the Immune Clearance of Platelets: A Transgenic Mouse Model", McKenzie et al., The Journal Immunology, pp. 4311-4318 (1999) vol. 162.
"Functional Consequences of the Interaction Between T-cell Antigen Receptors and FcγRs on T Cells", Kwack et al., Immunology Letters, 44 (1995) pp. 139-143, Elsevier Science B.V.

* cited by examiner

*Primary Examiner*—Anne M. Wehbe
(74) *Attorney, Agent, or Firm*—Sheridan Ross P.C.

(57) ABSTRACT

The present invention provides a FcγRIIa transgenic non-human animal model for autoimmune disease, particularly arthritis. This invention also provides a method of using this model to screen compounds that can reduce aberrant immune activity including aberrant immune complex formation aberrant immune complex clearance and immune complex induced inflammation. This invention also provides means of using this model to treat or prevent autoimmune disease.

18 Claims, 14 Drawing Sheets

FCγRIIA TRANSGENIC ANIMAL MODEL FOR AUTOIMMUNE DISEASE

This application is a national stage application under 35 U.S.C. 371 of PCT Application No. PCT/AU03/00718, filed Jun. 6, 2003, which published in English and designated the United States. PCT/AU03/00718 claims priority under 35 U.S.C. §119(a)-(d) and 35 U.S.C. 365(b) from Australian Application No. 2002950529, filed Aug. 1, 2002 and from Australian Application No. PS 2856, filed Jun. 7, 2002. The entire disclosure of each of the above-identified applications is incorporated herein by reference.

FIELD OF THE INVENTION

The present invention relates to a non-human transgenic animal model for autoimmune disease, particularly arthritis. The invention also relates to methods for identifying compounds that can reduce aberrant immune activity and immune complex associated inflammation. This invention also relates to methods for identifying a mode of autoimmune disease development and for the identification of compounds that ameliorate this and the processes associated with this that lead to disease.

BACKGROUND OF THE INVENTION

Receptors for the Fc domain of IgG (FcγRs) amongst other factors are known to play a role in the regulation of the immune system. Currently, three classes of FcγRs are distinguished on cells of the immune system: the high-affinity receptor FcγRI (CD64), capable of binding monomeric IgG; the low-affinity receptors FcγRII (CD32) and FcγRIII (CD16), which interact preferentially with complexed IgG. Although these receptors show overlapping binding patterns for IgG subclasses, they vary in their cellular effector functions. FcγRI, FcγRIIa and FcγRIIIa are activating receptors, characterised by the presence of an immunoreceptor tyrosine-based activation motif immunoreceptor tyrosine-based activation motif (ITAM), either in the cytoplasmic domain of the receptor (FcγRIIa) or associated with the receptor as an accessory signalling subunit (γ and/or β chains associated with FcγRI and FcγRIIIa). By contrast, FcγRIIb is an inhibitory receptor, containing an immunoreceptor tyrosine-based inhibitory motif (ITIM) in its cytoplasmic domain. A marked exception to this dichotomy is FcγRIIIb; this receptor is linked to the outer leaflet of the plasma membrane by a glycosyl phosphatidylinositiol (GPI) anchor and does not contain or associate with ITAMs or ITIMs. There is presently no homolog described for FcγRIIa or FcγRIIIb in mice.

Whilst FcγR:Ig interactions are important effector systems in immunity, their role in autoimmune disease is uncertain. In humans the major inflammatory cells—macrophages, neutrophils, eosinophils and mast cells are known to express FcR receptors, including FcγRI, FcγRIIa, FcγRIIb, and FcγRIIIa, or FcγRIIIb.

FcγRIIa is present only in humans and higher primates, so there is no equivalent in mice or other rodents. The receptor is of particular interest because of the dependence of other Fc receptors on this receptor for their signal transduction and cell activating properties (Chuang et al. 2000). FcγRIIa can be expressed in transgenic mice with the same expression pattern as in humans (McKenzie et al. 1999). Thus human FcγRIIa can interact appropriately with intracellular signalling pathways in the mouse and appear normal in all respects, although changes in cross-species regulation in transgenics should always be considered in interpreting results. Transgenic mice expressing the human FcγRIIa have shown that this receptor is a major factor in platelet destruction in immune thrombocytopenia (McKenzie et al. 1999). The role of FcR receptors in inducing cell activation is known for in vitro systems, but their role in inflammation in vivo is less understood and has recently been studied, as described herein.

As a result of the use of gene knock out animals, the scientific and medical communities believe that the principal receptor involved in the induction of inflammation in vivo is FcγRIII (also known as CD16). Many studies in the literature indicate this and this has formed part of recent text book descriptions of immune complex induced inflammation. It was therefore very surprising that transgenic mice expressing the human FcγRIIa are highly sensitive to immune complex induced inflammation, also spontaneously develop inflammation in a variety of organs and tissues characteristic of a number of autoimmune diseases such as rheumatoid arthritis, systemic lupus erthemotosus (SLE), induced autoimmune disease such as glomerular basement membrane nephritis. Moreover, mice that develop these surprising inflammatory sensitivities are also useful for testing drugs.

However, no studies have examined the role of this FcR in autoimmune disease, such as SLE, arthritis or any other immune complex disorders, for example, the role of this Fc receptor in immune complex or antibody induced inflammation associated with autoimmune diseases. Inflammation in these diseases can include vasculitis, lupus nephritis and arthritis. Inflammation can also occur in diseases not necessarily classified as autoimmune such as infectious arthritis, in renal diseases such as mixed cryoglobulinemia, bacterial infections, in malignant diseases, in gastrointestinal diseases, complement deficiencies and in a number of miscellaneous conditions.

Accordingly, there remains a need for providing effective methods and models for autoimmune disease and methods for identifying compounds that can reduce aberrant immune activity, inflammation and disease processes. The surprising observation of the increased sensitivity to collagen induced arthritis in the transgenic mice whose genetic make up is composed of genes from otherwise genetically resistant mice, together with the observation of a spontaneous autoimmune disease, including arthritis was surprising. More surprising was that on further analysis of the transgenic animals, evidence of spontaneous autoimmunity and inflammation in tissues was evident. Inflammation in kidneys and in lungs occurred in many, though not all mice and histological examination of the joints showed features characteristic of rheumatoid arthritis, i.e. bone destruction and panus formation or features more characteristic of arthritis associated with diseases such as SLE where panus does not form. It would appear therefore that the presence of human FcγRIIa receptor in these mice allows the development of quite different inflammatory processes in different tissues that make up different clinical diagnoses.

SUMMARY OF THE INVENTION

A first aspect of the present invention is a method for screening a compound that is able to suppress aberrant immune activity, the method comprising the steps of:

(a) administering a compound to be screened to a non-human transgenic animal that has been modified to express human FcγRIIa receptor such that the transgenic animal is susceptible to an autoimmune disease; and (b) assessing the transgenic animal to determine if the compound reduces aberrant immune activity in the animal.

Preferably, the compound can reduce aberrant immune activity, such as but not limited to, aberrant immune complex formation, aberrant immune complex clearance or immune complex induced inflammation in a subject. The method of the present invention preferably includes the additional step of (c) assessing the transgenic animal to determine if the compound reduces immune complex induced inflammation.

A preferred aspect of the present invention is a method for screening a compound that is able to suppress an autoimmune disease, the method comprising the steps of:

(a) administering a compound to be screened to a non-human transgenic animal that has been modified to express human FcγRIIa receptor such that the transgenic animal is susceptible to an autoimmune disease; and (b) assessing the transgenic animal to determine if the compound reduces aberrant immune activity in the animal.

The non-human transgenic animal is preferably resistant to collagen-induced arthritis prior to being modified to express the human FcγRIIa receptor. Preferably, the transgenic animal is a transgenic mouse derived from the strains C57BL/6 and SJL that has been modified to express human FcγRIIa receptor. The aberrant immune activity preferably includes aberrant immune complex formation, aberrant immune complex clearance or immune complex induced inflammation. Preferably, the compound is able to reduce aberrant immune activity in the animal by inhibiting the activity of FcγRIIa expressed in the animal. In step (b) of the method, the aberrant immune activity can be preferably assessed in terms of clinical symptoms and/or pathological features of an autoimmune disease, such as arthritis or systemic lupus erthematosus (SLE). Preferably, the autoimmune disease is an autoimmune disease other than thrombocytopenia. Preferably, the autoimmune disease may include systemic lupus erthematosus (SLE), Crohn's disease, mixed cryoglubulinemia and other conditions involving pathology due to immune complexes. More preferably, the autoimmune disease is rheumatoid arthritis (RA) or more preferably collagen-induced arthritis (CIA). The assessment step (b) may include suitable assays for assessing aberrant immune activity, such as a suitable antibody assay. Other assays include analysis of cytokine expression by immunohistochemistry, PCR or ELISA in situ or in circulation, immune function tests such as antigen presentation, biochemical tests such as cell signalling.

Another aspect of the present invention is a method for screening a compound that is able to suppress an autoimmune disease, the method comprising the steps of:

(a) administering a compound to be screened to a non-human cell expressing human FcγRIIa receptor, wherein the cell is derived from a non-human transgenic animal that has been modified to express human FcγRIIa receptor such that the transgenic animal is susceptible to an autoimmune disease; and (b) assessing the cell to determine if the compound reduces aberrant immune activity in the cell.

The non-human transgenic animal is preferably resistant to collagen-induced arthritis prior to being modified to express the human FcγRIIa receptor. Preferably, the transgenic animal is a transgenic mouse derived from the strains C57BL/6 and SJL that has been modified to express human FcγRIIa receptor. Preferably, the aberrant immune activity includes aberrant immune complex formation, aberrant immune complex clearance or immune complex induced inflammation. The compound is preferably able to reduce aberrant immune activity in the cell by inhibiting the activity of FcγRIIa expressed in the cell. The assessment step (b) may include suitable assays for assessing aberrant immune activity, such as suitable antibody assays. Other suitable assays include analysis of cytokine expression by immunohistochemistry chemistry, PCR or ELISA in situ or in circulation, immune function tests such as antigen presentation, biochemical tests such as cell signalling.

A further aspect of the present invention is a compound when identified by the screening methods of the present invention that can reduce aberrant immune activity in a cell or animal.

The invention also provides a method of treating or preventing an autoimmune disease in a subject, the method comprising administering an effective amount of a compound that can reduce aberrant immune activity in the subject.

Preferably, the compound can reduce aberrant immune complex formation, aberrant immune complex clearance or immune complex induced inflammation in a subject. Preferably, the compound is able to reduce aberrant immune activity in the cell by inhibiting the activity of FcγRIIa expressed in the subject. The compound used in the method is preferably identified by the screening methods of the present invention. Preferably, the autoimmune disease is caused by aberrant immune complex formation, aberrant immune complex clearance or immune complex induced inflammation. The autoimmune disease is preferably arthritis or systemic lupus erythematosus (SLE). Preferably, the autoimmune disease is rheumatoid arthritis (RA) or more preferably collagen-induced arthritis (CIA).

The present invention also provides a composition for treating or preventing an autoimmune disease, the composition comprising an effective amount of a compound that can reduce aberrant immune activity in an animal, and a pharmaceutically acceptable diluent, excipient or carrier.

Preferably, the compound in the composition is identified by the screening methods of the present invention. The autoimmune disease is preferably arthritis or systemic lupus erythematosus (SLE). Preferably, the autoimmune disease is rheumatoid arthritis (RA) or more preferably collagen-induced arthritis (CIA).

Another aspect of the present invention is a non-human transgenic animal that has been modified to express human FcγRIIa receptor such that the transgenic animal is susceptible to an autoimmune disease, wherein the transgenic animal is resistant to collagen-induced arthritis prior to being modified to express the human FcγRIIa receptor.

The transgenic animal is preferably a mammal, such as, but not limited to, a rodent, dog, cat, pig, rabbit or non-human primate. More preferably, the transgenic animal is a mouse. More preferably, the transgenic animal is a transgenic mouse derived from the strains C57BL/6 and SJL that has been modified to express human FcγRIIa receptor. Preferably, the autoimmune disease is caused by aberrant immune complex formation, aberrant immune complex clearance or immune complex induced inflammation. The autoimmune disease is preferably arthritis or systemic lupus erythematosus (SLE). Preferably, the autoimmune disease is rheumatoid arthritis (RA) or more preferably collagen-induced arthritis (CIA).

In a preferred aspect of the invention the non-human transgenic animal as hereinbefore described is used in a method to identify a molecule associated with FcγRIIa ligand binding or a molecule dependent on FcγRIIa ligand binding. Preferably, the non-human transgenic animal is used in a method to identify a molecule including, but not limited to, antagonists or agonists of a ligand of FcγRIIa.

The present invention further provides a method of producing a non-human transgenic animal model for autoimmune disease, the method comprising the steps of:

(a) introducing a nucleic acid molecule encoding human FcγRIIa receptor to a cell of a non-human embryo;

(b) transferring the embryo to a foster mother; and (c) assessing the resultant born animal for susceptibility to autoimmune disease;

wherein the non-human transgenic embryo is resistant to collagen-induced arthritis prior to the introduction of a nucleic acid molecule encoding a human FcγRIIa receptor.

The transgenic animal is preferably a mouse. More preferably, the transgenic animal is a transgenic mouse derived from the strains C57BL/6 and SJL that has been modified to express human FcγRIIa receptor. Preferably, the autoimmune disease is caused by aberrant immune complex formation, immune complex clearance or immune complex induced inflammation. The autoimmune disease is preferably arthritis or systemic lupus erythematosus (SLE). Preferably, the autoimmune disease is rheumatoid arthritis (RA) or more preferably collagen-induced arthritis (CIA).

The invention also provides a method for producing a composition for treating or preventing an autoimmune disease, the method comprising (a) selecting the compound by the method as hereinbefore described; and (b) formulating the compound with a pharmaceutically acceptable diluent excipient or carrier to produce the composition.

BRIEF DESCRIPTION OF THE ACCOMPANYING FIGURES

FIG. 1A shows feet of a mouse with typical spontaneous arthritis at >30 weeks. Features include swelling, redness and rigidity of the joints, compared with feet of a normal mouse as shown in FIG. 1(B).

FIG. 2 shows a mouse hind limb with spontaneous arthritis (2A) and a normal mouse hind limb (2D). Histological staining (H&E sections, 400× magnification) of the knee joints of the arthritic mouse are shown in 2B and 2C, compared with a normal knee joint from an aged matched non-transgenic mouse (2E), showing inflammation with synovium hyperplasia and infiltrated by cells in the arthritic joint (2B). In mice with spontaneous arthritis, pannus formation and cartilage destruction were seen (in 29% of mice at 20-40 weeks and 33% of mice at >40 weeks), with inflammatory infiltration of the cartilage (2B). Interestingly in the other mice with the spontaneous arthritis, histology showed synovitis with fewer inflammatory cells and no pannus formation more characteristic of arthritis associated with disease such as Systemic Lupus Erythematosus (FIG. 2C). FIG. 2F shows the % cumulative incidence of spontaneous arthritis at 20 and 40 weeks.

Figure 3:
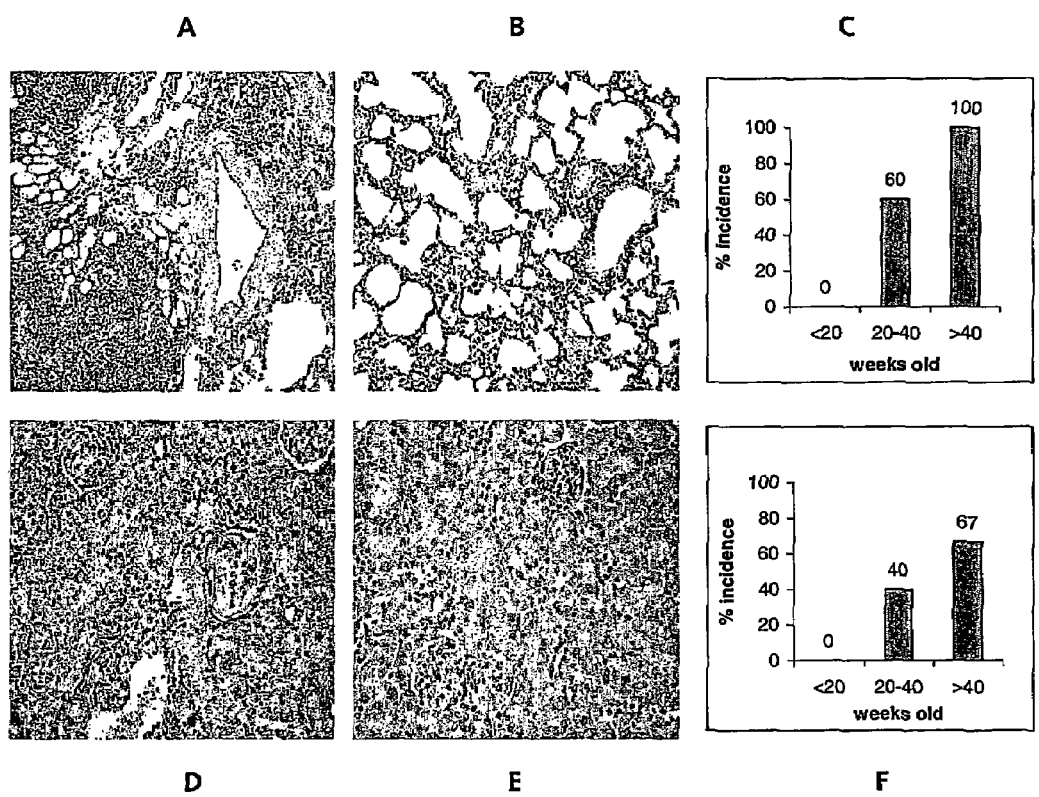
Figure 4:
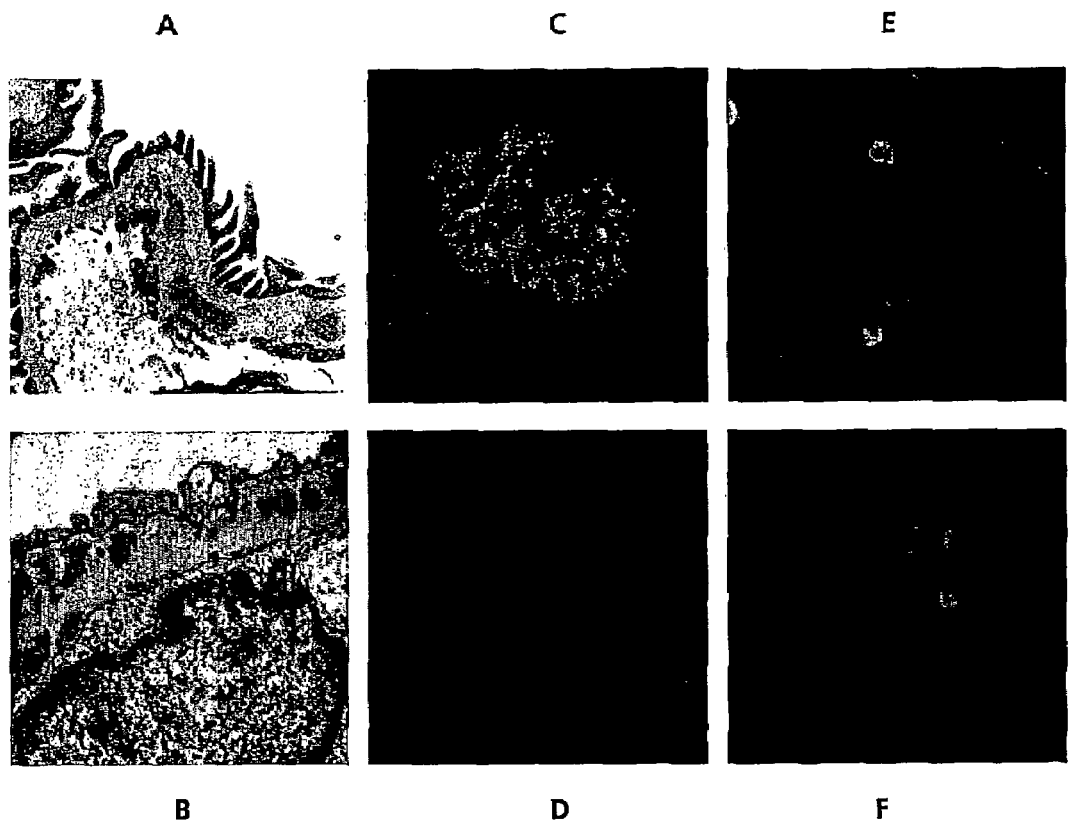

FIG. 3 shows that eexamination of the organs from >20 week old transgenic mice revealed symptoms of autoimmune disease, with some of the features commonly seen in rheumatoid arthritis or human Systemic Lupus Erythematosus (SLE) (Edworthy 2001). The abnormalities included: pneumonitis with perivascular inflammation (FIG. 3A compared with normal lungs 3B) in 60-100% of mice (FIG. 3C) and glomerulopathy (FIG. 3D compared with a normal kidney, 3E) in 40-67% of older mice (FIG. 3F).

FIG. 4A-F show electron microscopy. FIG. 4A shows electron microscopy of the kidneys from an old transgenic mouse, at the junction of the uriniferous space (us) and a capillary (cap), revealing irregular floccular electron density intra basement membrane, representative of immune complex for deposition and identical to that seen in human kidneys from end-stage SLE patients (FIG.4B). Intra-glomerular immuno- complex deposition in the kidney of a mouse with glomerulopathy was also detected by a fluorescein-conjugated anti-mouse IgG (FIG.4C). This was a feature not seen in aged matched non-transgenic mice (FIG. 4D). High titres of anti-nuclear antibody were detected in the sera from 83% of transgenic mice aged >20 weeks, staining the cell nucleus with the "homogeneous nuclear pattern." (FIG. 4E). The same pattern was observed with an anti-histone antibody (huPIA3) (FIG. 4F), indicating that at least one component of the anti-nuclear antibody detected in the transgenic mice was anti-histone. Anti-nuclear antibodies (ANA) with this staining pattern are found in 70-95% of SLE patient and are one of the indicators for SLE (Edworthy 2001). Unlike the other features of autoimmune disease, ANA was also detected at low levels in transgenic mice examined at 12 weeks, and in age matched non-transgenic controls. This parallels the human situation, where up to 30% of the population may have serum ANA with no symptoms of autoimmune disease. No antibodies for double stranded DNA were seen (data not shown). No lung or kidney disease was seen in age matched non-transgenic C57BL/6 or (C57BL/6 ×SJL)F$_1$ mice.

FIG. 5 shows that DBA/1 mice (H-2$^q$) immunised with collagen type II (CII) develops an arthritis. Collagen induced arthritis (CIA) disease development and severity in FcγRIIa transgenic mice (C5BL/6 and SJL genetic background) was compared with the CIA-resistant background strains (C57BL/6 (H-2$^b$) and C57BL/6×SJL F1 (H-2$^{b/s}$)) with the susceptible DBA/1 (H-2$^q$) mice. The FcγRIIa transgenic mice developed arthritis with more rapid onset (as early as day 20) and greater severity than in the susceptible DBA/1 mice. The non-susceptible strains did not develop arthritis. FIG. 5C: circles show CIA score in transgenic mice: squares show the score in DBA/1 mice, triangles show C57BL/6 mice. Histology of the joints from FcγRIIa, DBA/1, C57BL/6 and (C57BL/6×SJL) F$_1$ mice culled on day 36 post arthritis induction confirmed this diagnosis. FcγRIIa transgenic mice showed massive synovial inflammation (FIG. 5A) and some articular erosion, caused by invading inflammatory cells replacing normal articular cartilage, and the development of pannus in the joint (FIG. 5B). These lesions were also found in the DBA/1 mice, but not in the joints from non-susceptible strains such as C57BL/6. Pannus formation progressing to degradation of the extracellular matrix, is a common feature of joints in humans with rheumatoid arthritis.

FIG. 6 shows a graph indicating the incidence of spontantenous arthritis in FcγRIIa mice. The percentage % incidence at each time point is shown in grey and the cumulative prevalence % in mice (n=50) with disease is shown in black. Note that this is a much larger cohort of mice to those anlysed in FIG. 2.

FIG. 7 shows a graph of the level of arthritis index over time for CIA in mice (n=4) treated with only two doses of VIB 153 (7.5 mg/dose on days 21 and 27), no treatment (n=28) or mice (n=15) treated with 4 doses of VIB 153 (7.5mg/dose on days 21, 24, 27, 30). CIA was induced by intradermal injection of an emulsion formed by combining 2 mg/ml chicken collagen type II (Sigma, St Louis, Mo.) dissolved in 10 mM acetic acid in an equal volume of CFA. 100 µl of the emulsion was injected i.d. into the base of the tail. The same dose was prepared and administered proximal to the primary site 21 days later (Campbell et al. 1997).

FIG. 8 shows typical swelling, redness and rigidity of the ankle joints, in the feeto of a transgenic mouse with CIA (A), in contrast to the normal appearance of the feet of (B) a treated transgenic mouse (4 doses of VIB 153, 7.5 mg/dose on days 21, 24, 27, 30) at day 32.

Figure 9:
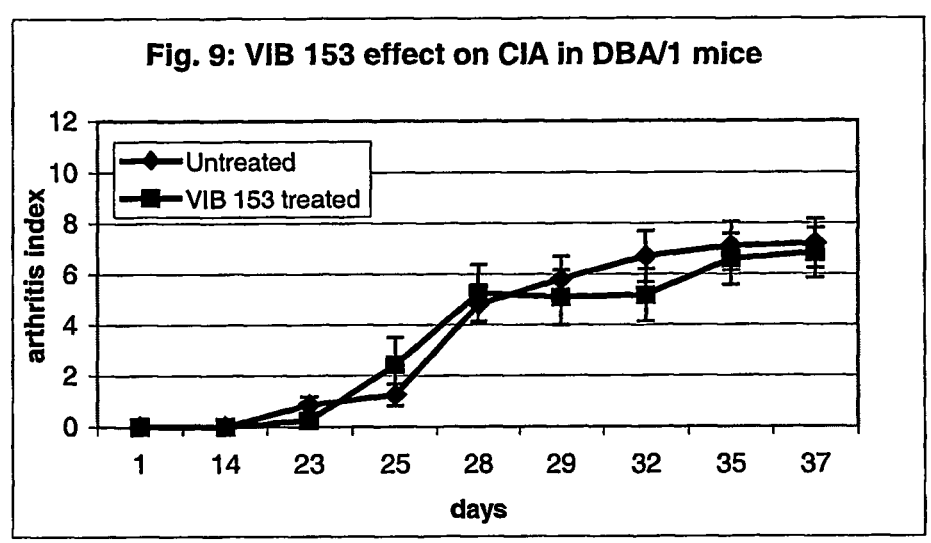
FIG. 9 shows a graph of level of arthritis index for CIA in non transgenic DBA/1 mice (n=12) treated with VIB 153 (4 doses, 7.5mg/dose on days 21, 24, 27, 30) or untreated mice (n=27), dearly demonstrating that VIB 153 is not effective in treating CIA in non-transgenic mice.

FIG. 9 shows a graph of level of arthritis index for CIA in non transgenic DBA/1 mice (n=12) treated with VIB 153 (4 doses, 7.5mg/dose on days 21, 24, 27, 30) or untreated mice (n=27), clearly demonstrating that VIB 153 is not effective in treating CIA in non-transgenic mice.

FIG. 10 and FIG. 11 show graphs of level of arthritis (index or score) for individual mice treated after arthritis was established (4 doses, 7.5mg/dose on days 21, 24, 27, 30) with the following drug compounds: 6727, 6728, VIB197 and VIB 153. This demonstrated that the drugs are effective in treating established arthritis when disease index is low.

FIG. 12 and FIG. 13 show graphs of the level of arthritis (index or score) in mice with CIA treated with the following drug compounds prior to disease onset: 6727, 6728, VIB197, VIB 153 (4 doses, 7.5 mg/dose on days 21, 24, 27, 30) or no treatment (n=6 mice/group).

FIG. 14 shows a graph of the level of arthritis index in FcγRIIa transgenic mice with CIA treated prior to disease onset with known immunisuppressive and nati-inflammatory agents anti-CD3 monoclonal antibody or methotrexate compared with controls (PBS treated).

DETAILED DESCRIPTION OF THE INVENTION

A first aspect of the present invention is a method for screening a compound that is able to suppress aberrant immune activity, the method comprising the steps of:

(a) administering a compound to be screened to a non-human transgenic animal that has been modified to express human FcγRIIa receptor such that the transgenic animal is susceptible to an autoimmune disease; and (b) assessing the transgenic animal to determine if the compound reduces aberrant immune activity in the animal.

Preferably, the compound can reduce aberrant immune activity, such as but not limited to, aberrant immune complex formation, aberrant immune complex clearance or immune complex induced inflammation in a subject. The method of the present invention preferably includes the additional step of:

(c) assessing the transgenic animal to determine if the compound reduces immune complex induced inflammation.

In a preferred aspect of the invention there is provided a method for screening a compound that is able to suppress an autoimmune disease, the method comprising the steps of:

(a) administering a compound to be screened to a non-human transgenic animal that has been modified to express human FcγRIIa receptor such that the transgenic animal is susceptible to an autoimmune disease; and (b) assessing the transgenic animal to determine if the compound reduces aberrant immune activity in the animal.

In the present specification the term "autoimmune disease" is to be understood to include a heterogeneous group of disorders in which the recognition of self antigens by lymphocytes is involved in pathogenic organ damage (for example see tables 22-1, 22-2 and 12-2 of Edworthy (2001). Antibodies and immune complexes can also be involved in tissue damage in disease not strictly autoimmune in nature. The term therefore includes diseases or conditions that are caused by aberrant immune activity. The phrase "aberrant immune activity" refers to abnormal immune function in a cell, such as but not limited to, aberrant antibody or immune complex formation, aberrant antibody or immune complex clearance or immune complex induced inflammation. Preferably, the aberrant immune activity includes elevated immune complex formation in a cell compared to normal cells. The aberrant immune activity may preferably include elevated levels of antibodies or immune complex clearance in a cell compared to normal cells. The autoimmune disease is preferably caused by aberrant immune complex formation. (see Edworthy, 2001).

Aberrant immune complex formation is typically characterised by the presence of soluble immune complexes, formation of complexes in situ, and the deposition of immune complexes in target organs. The autoimmune disease may be preferably caused by aberrant immune complex clearance. Aberrant immune complex clearance is typically characterised by the inability of phagocytes of the reticuloendothelial system to bind immune complexes via FcR. This can be due to abnormalities in or lack of phagocytic cells, aberrations of the FcR, or over-production of immune complexes due to uncontrolled anti-self antibody production.

The autoimmune disease is preferably arthritis or systemic lupus erythematosus (SLE). Preferably, the autoimmune disease is rheumatoid arthritis (RA) or more preferably collagen-induced arthritis (CIA). Other autoimmune diseases or inflammatory conditions associated with antibody or immune complex formation are listed in Table 12-2 of Edworthy (2001).

The non-human transgenic animal is preferably resistant to collagen-induced arthritis prior to being modified to express the human FcγRIIa receptor. Preferably, the transgenic animal is a transgenic mouse derived from the strains C57BL/6 and SJL that has been modified to express human FcγRIIa receptor. The aberrant immune activity preferably includes aberrant immune complex formation and/or aberrant immune complex clearance. Preferably, the compound is able to reduce aberrant immune activity in the animal by inhibiting the activity of FcγRIIa expressed in the animal.

In step (b) of the method, the aberrant immune activity can be preferably assessed in terms of clinical symptoms and/or pathological features of an autoimmune disease, such as but not limited to arthritis or systemic lupus erythematosus (SLE). Preferably, the autoimmune disease is an autoimmune disease other than thrombocytopenia. Preferably, the autoimmune disease may include systemic lupus erthematosus (SLE), Crohn's disease, mixed cryoglubulinemia and other conditions involving pathology due to immune complexes. More preferably, the autoimmune disease is rheumatoid arthritis (RA) and most preferably collagen-induced arthritis (CIA). Clinical symptoms of an autoimmune disease or aberrant immune activity can include pathological cellular or tissue indicators that are recognised to be associated with autoimmune disease. For instance, the severity of an autoimmune disease such as arthritis may be assessed by the level of inflammation or swelling of a joint of an animal. Tissue samples of an animal may be assessed for damage characteristic of autoimmune diseases, such as arthritis. For example, histological examination of tissue sections can be carried out to identify damage such as pannus formation, infiltration, cartilage and/or bone damage or erosion. Other indicators of inflammatory, or autoimmune disease, include leukocyte infiltration of target organs such as lungs, pancreas, salivary glands, lungs, bowel, skin, muscle, testes and eyes lesions. Intra glomerular immune complex deposition, associated with high titre anti-nuclear antibodies is detected by immunohistology and electron microscopy. Anti-nuclear antibodies, Rheumatoid factor and enzyme-specific antibodies (eg anti-insulin) can be detected in ELISA assays.

The assessment step (b) of the method of screening may include suitable assays for assessing aberrant immune activity, such as a suitable antibody assay. For instance, Systemic Lupus Erthematosus (SLE) is an autoimmune disease characterised by the development of antinuclear antibodies (ANA), especially against DNA. Therefore, antinuclear antibodies can be used to assay the level of ANAs in an animal to test for SLE. Other assays are listed in table 11-2 of Edworthy (2001). In an aspect of the present invention there is provided a method for screening a compound that is able to suppress an autoimmune disease, the method comprising the steps of:

(a) administering a compound to be screened to a non-human cell expressing human FcγRIIa receptor, wherein the cell is derived from a non-human transgenic animal that has been modified to express human FcγRIIa receptor such that the transgenic animal is susceptible to an autoimmune disease; and (b) assessing the cell to determine if the compound reduces aberrant immune activity in the cell.

The non-human transgenic animal is preferably resistant to collagen-induced arthritis prior to being modified to express the human FcγRIIa. Preferably, the transgenic animal is a transgenic mouse and more preferably of the C57BL/6 and genetic backgrounds that has been modified to express human FcγRIIa receptor. The mouse is characterised in the published paper by McKenzie et al. 1999, listed in references.

The aberrant immune activity preferably includes aberrant immune complex formation and/or aberrant immune complex clearance. The aberrant immune activity may be measured in a cell by preferably assessment in terms of clinical symptoms and/or pathological features of an autoimmune disease, such as arthritis or systemic lupus erythematosus (SLE). Preferably, the autoimmune disease is an autoimmune disease other than thrombocytopenia. Preferably, the autoimmune disease may include systemic lupus erthematosus (SLE), Crohn's disease, mixed cryoglubulinemia and other conditions involving pathology due to immune complexes. More preferably, the autoimmune disease is rheumatoid arthritis (RA) and most preferably collagen-induced arthritis (CIA). Clinical symptoms of an autoimmune disease or aberrant immune activity can include pathological cellular or tissue indicators that are recognised to be associated with autoimmune disease. For instance, the severity of an autoimmune disease such as arthritis may be assessed by the level of inflammation or swelling of a joint of an animal. Tissue samples of an animal may be assessed for damage characteristic of autoimmune diseases, such as arthritis. For example, histological examination of tissue sections can be carried out to identify damage such as pannus formation, infiltration, cartilage and/or bone damage or erosion. Other indicators of inflammatory autoimmune or connective tissue disease, include leukocyte infiltration of target organs such as lungs, pancreas, salivary glands, lungs, bowel, skin, muscle, testes and eye lesions. Intra glomerular immune complex deposition, associated with high titre anti-nuclear antibodies is detected by immunohistology and electron microscopy. Anti-nuclear antibodies, anti-collagen antibodies and Rheumatoid factor can be detected in by FACS and ELISA assays. Aberrant cytokine secretion (TNF-alpha, IL1, in RA) can be detected by ELISA, ELISPOT or RNAse protection assays. The assessment step (b) may include suitable assays for assessing aberrant immune activity, such as a suitable antibody assay. Anti-nuclear antibodies, anti-collagen antibodies and Rheumatoid factor can be detected in by FACS and ELISA assays.

The compound identified in the screening method of the present invention is preferably able to change aberrant immune activity in the cell by inhibiting the activity of FcγRIIa expressed in the cell. The compound may be an antagonist of FcγRIIa, such as an antibody against FcγRIIa or a soluble FcγRIIa protein fragment. Other suitable compounds that may be screened in the methods of the present invention may include naturally occurring compounds, such as but not limited to proteins and nucleic acid molecules, recombinant molecules or synthetic agents. The compound may be a Fc receptor modulating compound such as those described in U.S. Pat. No. 6,355,683 and WO 00/15214, the contents of which are herein incorporated. The compounds could also include antibodies, peptides, non natural peptides composed of non natural amino acids or non-natural bonds or synthesised using non natural synthetic methods or small chemical entities including inorganic and organic compounds or combinations thereof.

A further aspect of the present invention is a compound when identified by the screening methods of the present invention that can reduce aberrant immune activity in a cell or animal. Such compounds would be suitable as pharmaceutical agents in the treatment or prevention of autoimmune diseases. Moreover, the compounds identified by the methods of the present invention may be used in studies to further elucidate autoimmune disease.

The invention also provides a method of treating or preventing an autoimmune disease in a subject, the method comprising administering an effective amount of a compound that can reduce aberrant immune activity in the subject.

Preferably, the compound can reduce aberrant immune complex formation and/or aberrant immune complex clearance in a subject. Preferably, the compound is able to reduce aberrant immune activity in the cell by inhibiting the activity of FcγRIIa expressed in the subject. The compound used in the method is preferably identified by the screening methods of the present invention. Preferably, the autoimmune disease is caused by aberrant immune complex formation and/or aberrant immune complex clearance. The autoimmune disease is preferably arthritis or systemic lupus crythematosus (SLE). Preferably, the autoimmune disease is rheumatoid arthritis (RA) or more preferably collagen-induced arthritis (CIA).

In the method of the present invention, the term "effective amount" means a concentration of at least one compound sufficient to provide treatment or prevention of an autoimmune disease in a subject. The effective amount of a compound used in the methods of the present invention may vary depending on the subject and the type and level of autoimmune disease.

The subject treated by the methods of the invention may be selected from, but is not limited to, the group consisting of humans, sheep, cattle, horses, bovine, pigs, poultry, dogs and cats. The compound administered to a subject is preferably formulated as a pharmaceutical composition. The compound can be administered to humans and other animals orally, rectally, parentally (ie intravenously, intramuscularly, or subcutaneously), intracisternally, intravaginally, intraperitoneally, topically (as by powders, ointments, or drops), transdermally, bucally, or as an oral or nasal spray. Preferably, the compound is administered by injection to a tissue site of an autoimmune disease, such as a joint The injectable formulations can be sterilized, for example, by filtration through a bacterial-retaining filter, or by incorporating sterilizing agents in the form of sterile solid compositions which can be dissolved or dispersed in sterile water or other sterile injectable medium just prior to use. Solid dosage forms of the compounds for oral administration may include capsules, tablets, pills, powders, and granules. In such solid dosage forms, the active compound is mixed with at least one inert, pharmaceutically acceptable excipient or carrier such as sodium citrate or dicalcium phosphate and/or a) fillers or extenders such as starches, lactose, sucrose, glucose, mannitol, and silicic acid, b) binders such as, for example carboxymethylcellulose, alginates, gelatine, polyvinylpyrrolidone, sucrose, and acacia, c) humectants such as glycerol, d) disintegrating agents such as agar-agar, calcium carbonate, potato or tapioca starch, alginic acid, certain silicates, and sodium carbonate, e) solution retarding agents such as paraffin, f) absorption accelerators such as quaternary ammonium compounds g) wetting agents such as, for example, cetyl alcohol and glycerol monostearate, h) absorbents such as kaolin and bentonite clay, and i) lubricants such as talc, calcium stearate, magnesium stearate, solid polyethylene glycols, sodium lauryl sulfate, and mixtures thereof. In the case of capsules, tablets and pills, the dosage form may also comprise buffering agents.

Accordingly, the present invention also provides a composition for treating or preventing an autoimmune disease, the composition comprising an effective amount of a compound that can reduce aberrant immune activity in an animal, and a pharmaceutically acceptable diluent, excipient or carrier.

Preferably, the compound in the composition is identified by the screening methods of the present invention. The autoimmune disease is preferably arthritis or systemic lupus erythematosus (SLE). Preferably, the autoimmune disease is rheumatoid arthritis (RA) or more preferably collagen-induced arthritis (CIA).

The compositions of the present invention may be formulated as solutions and emulsions. Suitable excipients, such as emulsifiers, surfactants, stabilisers, dyes, penetration enhancers and anti-oxidants may also be present in the compositions. Suitable carriers that may be added in the compositions can include, water, salt solutions, alcohols, polyethylene glycols, gelatine, lactose, magnesium stearate and silicic acid. The compositions may include sterile and non-sterile aqueous solutions. The compositions are preferably in a soluble form and the compounds are preferably, diluted in a soluble sterile buffered saline or water solution. The compositions can also be formulated as suspensions in aqueous, non-aqueous or mixed media. Aqueous suspensions may further contain substances that increase the viscosity of the suspension and may also contain stabilisers. The solutions may also contain buffers, diluents and other suitable additives. The compositions can include other adjunct components that are compatible with the activity of the compounds. The compositions of the present invention may be formulated and used as foams, including emulsions, microemulsions, creams and jellies. The formulations of the above compositions described would be known to those skilled in the field of pharmacy.

The compositions may be in the form of solid dosage forms, such as tablets, drags, capsules, pills, and granules which can be prepared with coatings and shells such as enteric coatings and other coatings well known in the pharmaceutical formulating art. They may optionally contain opacifying agents and can also be of a composition that they release the active ingredient(s) only, or preferentially, in a certain part of the intestinal tract, optionally, in a delayed manner. Examples of embedding compositions which can be used include polymeric substances and waxes.

If desired, and for more effective distribution, the compounds can be incorporated into slow release or targeted delivery systems such as polymer matrices, liposomes, and microspheres. The compounds can also be in microencapsulated form, if appropriate, with one or more of the above-mentioned excipients. Liquid dosage forms of the compounds for oral administration may include pharmaceutically acceptable emulsions, solutions, suspensions, syrups and elixirs. In addition to the compounds, the liquid dosage forms may contain inert diluents commonly used in the art such as, for example, water or other solvents, solubilizing agents and emulsifiers such as ethyl alcohol, isopropyl alcohol, ethyl carbonate, ethyl acetate, benzyl alcohol, benzyl benzoate, propylene glycol, 1,3butylene glycol, dimethyl formamide, oils (in particular, cottonseed, groundnut, corn, germ, olive, castor, and sesame oils), glycerol, tetrahydrofurfuryl alcohol, polyethylene glycols and fatty acid esters of sorbitan, and mixtures thereof.

Besides inert diluents, the compositions of the present invention can also include adjuvants such as wetting agents, emulsifying and suspending agents, sweetening, flavouring, and perfuming agents. The composition of the present invention may be in dosage forms for topical administration of the compound, such a powders, sprays, ointments and inhalants. The compound may be mixed under sterile conditions with a pharmaceutically acceptable carrier and any needed preservatives, buffers, or propellants which may be required to provide a pharmaceutical composition.

Another aspect of the present invention is a non-human transgenic animal that has been modified to express human FcγRIIa receptor such that the transgenic animal is susceptible to an autoimmune disease, wherein the transgenic animal is resistant to collagen-induced arthritis prior to being modified to express the human FcγRIIa receptor.

The transgenic animal is preferably a mouse. More preferably, the transgenic animal is a transgenic mouse derived from the strains C57BL/6 and SJL that has been modified to express human FcγRIIa receptor. Preferably, the autoimmune disease is caused by aberrant immune complex formation and/or aberrant immune complex clearance. The autoimmune disease is preferably arthritis or systemic lupus erythematosus (SLE). Preferably, the autoimmune disease is rheumatoid arthritis (RA) or more preferably collagen-induced arthritis (CIA).

The present invention further provides a method of producing a non-human transgenic animal model for autoimmune disease, the method comprising the steps of:

(a) introducing a nucleic acid molecule encoding human FcγRIIa receptor to a cell of a non-human embryo;

(b) transferring the embryo to a foster mother; and (c) assessing the resultant born animal for susceptibility to autoimmune disease;

wherein the non-human transgenic embryo is resistant to collagen-induced arthritis prior to the introduction of a nucleic acid molecule encoding a human FcγRIIa receptor.

The transgenic animal is preferably a mouse. More preferably, the transgenic animal is a transgenic mouse derived from the strains C57BL/6 and SJL that has been modified to express human FcγRIIa receptor. Preferably, the autoimmune disease is caused by aberrant immune complex formation and/or immune complex clearance. The autoimmune disease is preferably arthritis or systemic lupus erythematosus (SLE). Preferably, the autoimmune disease is rheumatoid arthritis (RA) or more preferably collagen-induced arthritis (CIA). The mouse is characterised in the published paper by McKenzie et al. 1999.

Throughout this specification the word "comprise", or variations such as "comprises" or "comprising", will be understood to imply the inclusion of a stated element, integer or step, or group of elements, integers or steps, but not the exclusion of any other element, integer or step, or group of elements, integers or steps.

The invention will hereinafter be described by way of the following non-limiting Figures and Examples.

EXAMPLE 1

Methods for Using a Transgenic Mouse Model for Autoimmune Disease (a) Transgenic Mice Expressing Human IgG Receptor FcγRIIa.

In transgenic mouse models of the present invention the following mice strains were used DBA/1 (H-2$^q$) males at 8-12 weeks old, C57BL/6 (H-2$^b$) and (C57BL/6×SJ (H-2$^{b/s}$) males or females at 8-15 weeks old, and transgenic mice expressing the FcγRIIa human transgene on platelets, neutrophils and macrophages at physiological levels, (as described in McKenzie et al. 1999). Transgenic males or females at 12-15 weeks old were used in collagen-induced arthritis (CIA) experiments, and >25 weeks old for the spontaneous autoimmune disease studies. All mice were bred and kept in clean conditions and were fed a standard diet and water ad libitum. The mouse is characterised in the published paper by McKenzie et al. 1999, listed in references.

(b) Collagen Type II Preparation.

Complete Freund's Adjuvant (CFA) was prepared by mixing 100 mg heat-killed *M tuberculosis* H37 Ra (Difco Laboratories, Detroit, Mich.) ground in 20 ml Incomplete Freund's Adjuvant (Difco Laboratories, Detroit, Mich.). An emulsion was formed by combining 2 mg/ml chicken collagen type II (Sigma, St Louis, Mo.) dissolved in 10 mM acetic acid in an equal volume of CFA. 100 µl of the emulsion was injected i.d. into the base of the tail. The same dose was prepared and administered proximal to the primary site 21 days later (Campbell et al. 1997).

(c) Clinical Assessment of Arthritis.

Mice were examined 2-3 times per week from day 14 onwards. The severity of arthritis was rated on a scale from 0 to 3 for each extremity based on the swelling, redness, and the joint function. Score 0=normal, 1=mild swelling and/redness, 2=severe swelling and redness, 3=severe swelling and redness accompanied by joint dysfunction. The score of each mouse was calculated for the four limbs (maximum total score of 12 for each mouse) (Campbell et al. 1997).

(d) Assay for the Anti-Nuclear Antibodies (ANAs).

ANA tests were performed on Chinese Hamster Ovary (CHO) cells adhered to a Lab-Tek Chamber 8 well slide (Nunc, Naperville, Ill.) for 5 hours at 37° C. The cells then were fixed with 100% acetone for 5 min at room temperature, and washed 2 times with PBS/0.5% BSA. The cells were then incubated with mouse serum or anti-histone antibody raised in mice (antibody HuPIA3; cell line name 410.9D6A3 (Cosgrove 1987)) at various dilutions for 30 min on ice, followed by sheep anti-mouse IgG (Fab'2fragment)-FITC (Silenus, Melbourne, Australia) for 30 min on ice in the dark. For the staining shown in FIG. 4E serum was diluted 1:1000 and FIG. 4F anti-histone antibody in ascites was diluted 1:500.

(e) Histopathology Assessment.

At the end of experiments, the mice were culled and the organs were collected. Kidneys, lungs, and various other tissues were fixed with 10% formalin/PBS and embedded in paraffin. Sections (4-6 µm) were stained with hematoxylin and eosin. To detect immune complex deposition, kidney sections were stained with sheep anti-mouse IgG (Fab'2 fragment)-FITC (Silenus, Melbourne, Australia)

Joint tissues were decalcified before paraffin embedding with a solution containing 5% HCl, 3.5% acetic acid glacial, 95% ethanol, and 12.5% chloroform. Decalcification was considered complete when joints were bleached and flexible.

Sections (4-6 µm) were stained with hematoxylin and eosin and examined for histological changes associated with arthritis (pannus formation, infiltration, cartilage and bone damage).

(f) Electron Microscopy Assessment

Samples of kidney were cut into 1-2 mm cubes using razor blades, and then fixed by immersion in fixative containing 2-8% paraformaldehyde, 2-5% glutaraldehyde in 0.15 M cacodylate buffer at pH 7.4. After fixation for a minimum of 6 hours at 4° C., tissues were rinsed in cacodylate buffer and post-fixed in 1% osmium tetroxide, in 0.15 M cacodylate buffer, pH 7.4 for 2 hours at room temperature. Samples were then washed in distilled water and dehydrated in 10% incremental concentrations of acetone prior to embedding in Procure-Araldite resin. During the dehydration procedure, tissues were stained en-block using a solution of 2% uranyl acetate in 70% acetone. Ultra thin sections were cut on a cryostat using glass knives and stained with 5% uranyl acetate in aqueous solution for 30 minutes at room temperature, followed by Reynolds lead citrate for 10 minutes. Ultra thin sections were examined in a Philips 300 electron microscope at 60 KV. * All reagents were from ProSciTech Australia.

(g) Antibody Detection.

Serum levels of total IgG and anti-collagen type II antibodies were assayed using ELISA using standard techniques. Briefly 96well Seroduster "U" vinyl plates (Costar, Cambridge, Mass.) were coated over night at 4° C. with 50 µl/well of 50 µg/ml collagen type II in 10 mM acetic acid. The plates were blocked with 2% BSA in PBS for 1 hour at room temperature. Mouse test sera were serial diluted and added to each well. The antibody bound to the plates was then detected by secondary sheep anti-mouse IgG (Fab'2fragment)-HRP (Amersham LIFESCIENCE, Buckinghamshire, England) and developed using ABTS (Boehringer Mannheim, Rockville, Md.). The absorbance at 405 nm was measured by an ELISA microreader.

(h) Statistical Analysis.

Data expressed as mean +/− SEM were compared using Student's test.

EXAMPLE 2

Results from a Spontaneous Arthritis (SA) Mouse Model

Spontaneous arthritis was observed in 47% of FcγRIIa transgenic mice at >20 weeks of age, increasing to 58% of mice aged >40 weeks and manifesting as swelling and reddening of the footpads and stiffening of the digits, knees and ankles (FIG. 1A, compared with aged matched control, FIG. 1B). Histological examination of the limbs confirmed the diagnosis of arthritis, shown in FIGS. 2B and 2C (compared with normal limbs from age matched non-transgenic mice (FIG. 2E)) revealed inflammation with synovium hyperplasia and infiltration by polymorphonuclear cells. In most of the cases with spontaneous arthritis, pannus formation and cartilage destruction were seen, with inflammatory infiltration of the cartilage (FIG. 2B). However, in about one third of mice with the spontaneous arthritis, histology showed sub acute synovitis, less inflammatory cells and no pannus formation (FIG. 2C). FIG. 2F shows the % cumulative incidence of spontaneous arthritis at 20 and 40 weeks, with pannus formation in 29% at 20 weeks and 33% at >40 weeks.

Examination of the organs from these and other >20 week old transgenic mice revealed symptoms of autoimmune connective tissue disease, with some of the features commonly seen in human Systemic Lupus Erythematosus (SLE) (Edworthy 2001). The abnormalities included pneumonitis with perivascular inflammation in 60-100% of mice (FIGS. 3A, 3C) and glomerulopathy in 40-67% (FIGS. 3D, F). Intraglomerular immune complex deposition in the latter was detected by fluorescein-conjugated anti-mouse IgG (FIG. 4C); a feature not seen in aged matched non-transgenic mice (FIG. 4D). Electron microscopy of the kidneys from old transgenic mice (FIG. 4A) confirmed the immunohistochemistry, showing irregular floccular electron density intra basement membrane, representative of immune complex deposition and identical to that seen in human kidneys from end-stage SLE patients (FIG. 4B). Despite extensive kidney damage in older mice, increased proteinuria was not detected in these mice compared with non-transgenic older mice (data not shown). However, the onset of proteinuria in some autoimmune glomerulonephritis animal models apparently does not correlate with the sequale of glomerulonephritis and renal failure (Clynes, Dumitru et al. 1998). No lung or kidney disease was seen in age matched non-transgenic C57BL/6 or (C57BL/6×SJL)F$_1$ mice (FIGS. 3B and E) and none of the other organs examined (salivary gland, pancreas, gut, brain, heart, lymph nodes, spleen, skin eyes) showed abnormalities in either transgenic or non-transgenic mice.

Transgenic expression of activation-linked FcγRIIa clearly alters immune function in mice, making them susceptible to spontaneous immune complex disease. The observation of multiple symptoms of spontaneous immune complex disease in these mice provides the first direct evidence of a key role for this receptor in the development of such tissue specific autoimmune disease.

The present results show that spontaneous immune complex associated disease, manifesting initially as arthritis, was seen in mice carrying the human FcγRIIA gene. Non-transgenics on the same genetic background never developed disease at this age. These mice showed evidence of other immune complex mediated autoimmune reactivity, with high serum levels of anti-nuclear antibodies and immune complex deposition in the kidneys. Arthritis was characterised by inflammation of the synovium, with synovium hyperplasia, edema, cellular infiltration, and neovascularisation, leading to the formation of finger-like projections over the cartilage. This feature (pannus) is unique to rheumatoid arthritis and leads to chondrocyte breakdown, cartilage erosion and, eventually, bone reabsorption. Inflammation is stimulated by macrophage secretion of IL-1 and TNF alpha, leading to nitrous oxide and collagenase secretion, and chondrocyte death. T cell mediated induction of autoantibodies includes rheumatoid factor (RF), against the Fc portion of IgG. This is mostly IgM and seen in 70-90% of RA patients. Other autoantibodies, to collagen type II (the major cartilage component) and to keratin, are specifically diagnostic but not seen in all patients. FcγRIIa transgenic mice with spontaneous arthritis, show most of the above features at >25 weeks of age, providing evidence for the first time that expression of this FcR is involved in disease development.

EXAMPLE 3

Assessment of Systemic Lupus Erythematosus (SLE)

Systemic Lupus Erythematosus (SLE) is an autoimmune disease characterised by the development of antinuclear antibodies (ANA), especially against DNA. Antibodies to red and white blood cell surface antigens also develop, leading to anemia, thrombocytopenia, leukopenia, endothelial cell damage and vasculitis. Nerve damage is also seen. Renal failure and ultimately multiple organ failure are the end result. Many of these symptoms were seen in the aging FcγRIIa mice in that they also develop glomerulonephritis, pneumonitis and antinuclear antibodies. No mice were positive for rheumatoid factor. Detection of anti-nuclear antibodies which are symptoms of SLE were assessed in the following manner. High titres of anti-nuclear antibody were seen in 83% of the sera from transgenic mice aged >20 weeks, staining the cell nucleus with the "homogenous nuclear pattern". The same pattern was observed with an anti-histone antibody (huPlA3) (FIGS. 4E and 4F), indicating that the anti-nuclear antibody detected was anti-histone. Anti-nuclear antibodies with this staining pattern are found in 70-95% of SLE patients and are one of the indicators for SLE, although not diagnostic of the disease (Edworthy 2001). Unlike the other features of autoimmune disease, ANA was also detected in transgenic mice examined at 12 weeks, and in age matched non-transgenic controls. This parallels the human situation, where up to 30% of the population may have serum ANA with no symptoms of autoimmune disease. No antibodies for double stranded DNA, were seen (data not shown).

A summary of symptoms and disease incidence is shown in Table 1. As mentioned above, ANA appeared before other indicators of autoimmune disease, but was not clearly associated with disease development, since it was also seen in older non-transgenic animals. Of the 23 transgenic mice examined at >20 weeks, 19 (83%) had other symptoms of connective tissue disease. Of the disease free mice, 3 were aged 21-40 weeks and one was >40 weeks. Glomerulonephritis (Gn), with or without pneumonitis (Gn/Pn) was the most frequently observed disease: of 16 mice with these symptoms, 8 had Gn/Pn with no arthritis, 8 had arthritis and 5 of these had pannus. Gn severity increased with age but arthritis scores did not, with swelling and redness declining with time, although the joints remained stiff. Only one mouse (examined at 30 weeks) had all symptoms (ANA, Gn, arthritis, pannus). Three mice had arthritis only, and two of these showed pannus formation. Thus, these Gn/Pn and arthritis symptoms seem to develop independently. As expected, pannus development was dependent on arthritis (11 mice had arthritis: in 7 of these pannus was observed).

TABLE 1

| Disease and Symptoms* Summary | | | | | | | |
|---|---|---|---|---|---|---|---|
| Normal mice C57Bl/6 (M) C57Bl/6×SJL (F1) | Sex | age culled (weeks) | ANA | dsDNA | Arthritis Score | Pannus | Kidney GN | Pneumonitis |
| M#1 | | 25 | − | − | 0 | − | − | − |
| M#2 | | 25 | + | − | 0 | − | − | − |
| M#old | | >35 | + | − | 0 | − | − | − |

TABLE 1-continued

Disease and Symptoms* Summary

| | | | | | | | |
|---|---|---|---|---|---|---|---|
| M#1a | 32 | – | – | 0 | – | – | – |
| M#2b | 32 | + | – | 0 | – | – | – |
| F1#1 | >44 | – | – | 0 | – | | |
| F1#2 | >44 | – | – | 0 | – | | |
| F1#3 | >52 | + | – | 0 | – | | |

| Transgenic mice Group 1: <20 weeks | Sex | age culled (weeks) | ANA | dsDNA | Arthritis Score | Pannus | Kidney GN | Pneumonitis |
|---|---|---|---|---|---|---|---|---|
| S4.0.2 | M | 12 | – | – | 0 | – | – | |
| S4.0.3 | M | 12 | + | – | 0 | – | – | |
| S4.0.1 | M | 12 | + | – | 0 | – | – | |
| S4.0.4 | M | 12 | + | – | 0 | – | – | |

| Transgenic mice Group 2: 21-40 weeks | Sex | age culled (weeks) | ANA | Arthritis Score | Pannus | Kidney GN | Pneumonitis |
|---|---|---|---|---|---|---|---|
| S3.9N.13 | F | 25 | | 0 | – | +++ | + |
| S3.5.17 | F | 32 | + | 0 | – | – | |
| S3.1.1 | M | 35 | – | 0 | – | – | |
| S3.1.2 | M | 36 | + | 0 | – | – | |
| S3.4.14 | M | 37 | + | 0 | – | –/+ | |
| S3.4.11 | M | 38 | + | 0 | – | + | |
| S3.4.16 | M | 38 | – | 0 | – | –/+ | |
| S3.7.4 | M | 36 | | 3 | – | ++ | |
| S3.1.5 | M | 36 | – | 6 | – | – | |
| S2.1 | | 30 | + | 10 | + | +++ | |
| S8.0.3 | F | 31 | | 10 | + | + | – |
| ITP6.3 | | 25 | + | 11 | – | – | – |
| S8.0.2 | F | 32 | + | 12 | + | + | + |
| S8.0.1 | F | 40 | + | 12 | + | – | + |

| Transgenic mice GROUP 3: >40 weeks | Sex | age culled (weeks) | ANA | Arthritis Score | Pannus | Kidney GN | Pneumonitis |
|---|---|---|---|---|---|---|---|
| S3.2.8 | F | 52 | | 0 | – | ++ | |
| S3.6.76 | F | 52 | + | 0 | – | +++ | + |
| S7#2 | F | 54 | + | 0 | – | +++ | |
| S3.2.6 | F | 52 | + | 0 | – | – | |
| S3.2.5 | F | 52 | | 0 | – | +++ | |
| S7#1 | F | 47 | + | 4 | – | – | |
| S7#3 | F | 54 | + | 5 | + | –/+ | |
| S7#4 | F | 54 | + | 10 | + | ++ | |
| S3.2.7 | F | 52 | + | 10 | + | – | + |

ANA, pannus and pneumonitis results are presented as positive (+) or negative (–).
Arthritis scores were calculated as described above (score from 0-12).
Kidney disease was scored as absent (–), mild (–/+), moderate (++), or severe (+++).

ANA appeared before other indicators of autoimmune disease, but was not clearly associated with disease development, since it was also seen in older non-transgenic animals. Of the 23 transgenic mice examined at >20 weeks, 19 (83%) had other symptoms of disease. Of the disease free mice, 3 were aged 21-40 weeks and one was >40 weeks. Glomrulonephritis (Gn), with or without pneumonitis (Gn/Pn) was the most frequently observed disease: of 16 mice with these symptoms, 8 had Gn/Pn with no arthritis, 8 had arthritis and 5 of these had pannus. Gn severity increased with age but arthritis scores did not with swelling and redness declining with time, although the joints remained stiff. Only one mouse (examined at 30 weeks) had all symptoms (ANA, Gn, arthritis, pannus). Three mice had arthritis only, and two of these showed pannus formation. Thus, these Gn/Pn and arthritis symptoms seem to develop independently. As expected, pannus development was dependent on arthritis (11 mice had arthritis—7 of these pannus was observed).

EXAMPLE 4

Results from a Collagen-Induced Arthritis (CIA) Mouse Model

CIA disease development and severity were compared in FcγRIIa transgenic mice with the CIA-resistant background strains (C57BL/6 H-2$^b$ and (C57BL/6×SJL)F1, H-2$^{b/s}$) and with the CIA susceptible DBA/1 (H-2$^q$) mice. In contrast to the background strains, that did not develop CIA, the FcγRIIa transgenic mice developed arthritis with more rapid onset (as early as day 20) and greater severity than in DBA/1 mice (FIG. 5C). Histology of the joints from FcγRIIa, DBA/1, C57BL/6 and (C57BL/6×SJL)F1 mice culled on day 36 post arthritis induction confirmed this diagnosis. FcγRIIa transgenic mice showed massive synovial inflammation (FIG. 5A) and some articular erosion, caused by invading inflammatory cells replacing normal articular cartilage, and the development of pannus in the joint (FIG. 5B). These lesions were also found in the DBA/1 mice, but not in the joints from non-susceptible strains such as C57BL/6. Pannus formation, due initially to the proliferation of fibroblast-like cells between articular surfaces, and progressing to degradation of the extracellular matrix, is a common feature of joints in humans with rheumatoid arthritis (Harris 2001). The results show that collagen-induced arthritis in FcγRIIa mice shows earlier onset and greater severity of disease than in DBA/1 mice.

EXAMPLE 5

Results of Anti-Collagen II Antibody and Rheumatoid Factor Detection

The titre of anti-collagen II antibody in the serum of transgenic, DBA/1 and C57BL/6 mice was measured by ELISA. Even though arthritis development was observed earlier in the FcγRIIa transgenic mice, they had lower antibody titres (detected at day 21 and day 36) than DBA/1 or C57BL/6 mice. These results suggest that inflammatory responses in the FcγRIIa transgenic mice are activated by low titre anti-collagen antibody, leading to rapid, early induction of arthritis. ELISA assays for antibodies to IgG, ie Rheumatoid factor (RF), gave no positive results. RF is normally not detected in mice with CIA.

EXAMPLE 6

Results from the Spontaneous Arthritis (SA) Model

The transgenic mice used in this study expressed a uniquely human receptor for IgG, FcγRIIa, on the same cells and at physiological levels similar to that observed in humans. As they aged (>25 weeks) the mice developed spontaneous arthritis (SA), and showed abnormalities such as high titre anti-nuclear antibodies, inflammatory lung lesions and glomerulonephritis with intra-glomerular immune complex deposition. This study demonstrates a clear role for the human FcγRIIa in the development of immune complex disease in this mouse model system. FIG. 6 shows the % incidence of new disease at each time point (grey) and the cumulative prevalence % of mice (n=50) with disease (black).

The findings demonstrate that spontaneous arthritis is attributable to the expression of human FcγRIIa. As shown in FIG. 6, mice at 9-55 weeks of age were examined regularly for the development of arthritis.

Histological examination was performed on tissue samples (kidneys, lungs, and various other tissues) collected at 9-55 weeks of age and fixed with 10% formalin/PBS and embedded in paraffin. Sections (4-6 μm) were stained with hematoxylin and eosin. To detect immune complex deposition, kidney sections were stained with sheep anti-mouse IgG (Fab'2 fragment)-FITC (Silenus, Melbourne, Australia). Joint tissues were decalcified before paraffin embedding with a solution containing 5% HCl, 3.5% acetic acid glacial, 95% ethanol, and 12.5% chloroform. Decalcification was considered complete when joints were bleached and flexible. Sections (4-6 μm) were stained with hematoxylin and eosin (H&E) and diseased joints showed the histological changes characteristic of arthritis (pannus formation, infiltration, cartilage and bone damage). FIG. 2 shows H&E stained sections of, (E): a normal knee joint and, (B): an arthritic knee joint from an SA mouse showing cartilage erosion and pannus formation.

EXAMPLE 7

Collagen-Induced Arthritis in a Transgenic Mouse Strain Expressing Human FcγRIIa In younger mice (8-12 weeks), the presence of the FcγRIIa gene in a mouse strain of mixed genetic background (C57BL/6/SJL, H-2$^{b/s}$) that is normally resistant to collagen-induced arthritis (CIA), conferred susceptibility to this disease. Furthermore, these mice showed earlier onset of CIA than DBA/1 (H-2$^q$) mice, a known susceptible strain (see below). CIA was induced in mice by i.d. injection of an emulsion of chicken collagen type II in Complete Freund's Adjuvant (CFA) into the base of the tail. Two injections were given, on day 0 and 21 of the experiment. The severity of arthritis was rated on a scale from 0 to 3 for each limb extremity based on swelling, redness, and the joint function.

Score 0=normal,
1=mild swelling and/redness of footpads or digits,
2=severe swelling and redness of footpads and digits,
3=severe swelling and redness accompanied by joint dysfunction.

The score for each mouse was calculated by adding the scores of the four limbs (maximum score of 12 for each mouse) (Campbell et al. 1997).

The findings show that expression of the FcγRIIa transgene in mice results in disease susceptibility in a previously resistant strain, with greater disease severity and earlier onset than mice with a susceptible background. Thus the addition of FcγRIIa not only converted the CIA non-susceptible mice background into a susceptible strain, but also induced autoimmune disease closely resembling human rheumatoid arthritis and/or SLE in older mice, a disease not previously reported in the founding mouse strains (C57BL/6 or SJL). The results demonstrate that FcγRIIa plays an important role in the autoimmune disease development, in particular Rheumatoid Arthritis and SLE. Strategies that result in the blocking or down regulating of this receptor will also provide a promising therapeutic approach to inhibit autoimmune disease, such as Rheumatoid Arthritis and SLE, in humans.

EXAMPLE 8

Testing of Compounds in Mice with Collagen-Induced Arthritis

In control mice (n=28), over a period of 37 days disease progressed and resulted in a mean score of 7.5 (FIG. 7). No further increase in disease severity was seen from this time to >60 days. Mice (n=15) treated with four 7.5 mg doses of VIB 153 administered intra-peritoneally, commencing on day 21 (treated on day 21, 24, 27, 30), (FIG. 7) and examined until >60 days, showed no disease until day 37 and only one mouse developed mild disease during this time. Mice treated with only two doses of VIB 153 (7.5mg/dose on days 21 and 27) also showed very low levels of disease by day 37. Treated mice from the 4 dose group showed no signs of disease progression at >60 days. In the untreated mice, the swelling decreased over time, but the paws remained stiff and immobile at >60 days. Again, diseased joints showed the histological changes associated with arthritis (pannus formation, infiltration cartilage and bone damage), very similar to that seen with SA (see FIG. 5). FIG. 8 shows typical swelling and deformity in an untreated foot (A), in contrast to the normal appearance of the foot of a treated mouse (B) at day 32.

In a non-transgenic strain of mice that is susceptible to CIA (DBA/1) control mice (untreated) (n=27) were found to develop CIA over time, with a mean arthritis index of 7 at 37 days. Mice (n=12) treated with three 7.5mg doses of VIB 153 on days 21, 24 and 27 also developed CIA, and by day 37 the disease was of similar severity to that of the controls (see FIG. 9), showing that this drug has no effect when the transgene is absent.

EXAMPLE 9

Additional Testing of Compounds in a Collagen-Induced Arthritis Mouse Model

Mice with spontaneous arthritis at >30 weeks that were treated with three 7.5 mg doses of VIB 153 on days 0, 7, 14 after arthritis was observed had decreased swelling and redness at the end of treatment (mean scores reduced to 4, compared with 6 for untreated controls) but progression to joint stiffness was not prevented. Individual variation in this group of mice (n=3) was considerable, caused by the severity of disease at time of treatment Mice with higher scores were less amenable to treatment.

In mice with CIA, some developed disease prior to drug treatment (after the first collagen injection). These were treated with the same doses of drug as disease-free mice. Again, individual variation in this group of mice (n=2 mice/drug) was considerable, and depended on the severity of disease at time of treatment Mice with higher scores were less amenable to treatment (FIGS. 10 and 11).

CIA was induced in mice by i.d. injection of an emulsion of chicken collagen type II in Complete Freund's Adjuvant (CFA) into the base of the tail. Two injections were given, on day 0 and 21 of the experiment. The severity of arthritis was rated on a scale from 0 to 3 for each limb extremity based on swelling, redness, and the joint function.

Score 0=normal,

1=mild swelling and/redness of footpads or digits,

2=severe swelling and redness of footpads and digits,

3=severe swelling and redness accompanied by joint dysfunction.

The score for each mouse was calculated by adding the scores of the four limbs (maximum score of 12 for each mouse) (Campbell et al. 1997).

Mice were treated with four 7.5 mg doses of drug administered intra-peritoneally, commencing on day 21 (treated on day 21, 24, 27, 30), and examined until >60 days (see FIG. 12 and 13. In the untreated mice, the swelling decreased over time, but the paws remained stiff and immobile at >60 days. Again, diseased joints showed the histological changes associated with arthritis (pannus formation, infiltration, cartilage and bone damage), very similar to that seen with SA. All of the drugs tested (6727, 6728, VIB197, VIB 153) modified the development of CIA, either delaying the onset of disease or reduce severity significantly, with low scores maintained for >30 days.

It is clear from these studies that the presence of FcRIIa confers sensitivity to immune complexes on these mice despite there being all the other activating and inhibitory Fc receptors—FCRI and FcRIII as well as FcRIIb—present in these mice. It would therefore be expected that in diseases other than autoimmune diseases such sensitivity to antibodies and inflammation caused by antibodies and immune complexes would be evident in FcγRIIa transgenic mice and would be useful for testing compounds to potentially treat these diseases.

EXAMPLE 10

Treatment of CIA with Anti-T Cell or Anti-Inflammatory Agents

T cells are known to play a significant role in the induction of CIA. For instance, T cell inactivation with an anti-CD3 monoclonal antibody (KT3), that recognises the T cell receptor chain, before the onset of CIA in DBA/1 mice has been shown to reduce disease severity (Hughes, Wolos et al. 1994). In the present study anti-CD3 antibody was used at a dose that is known to be immunosuppressive in mice (Mottram, Murray-Segal et al. 2002), to treat FcγRIIa transgenic mice with induced CIA. CIA was induced in mice as described in Example 7, then the mice were treated on day 20, before disease onset and prior to the second collagen injection (day 21) and again on days 22, 23 and 25 with 0.5mg ip of anti-CD3. As reported for DBA/1 mice (Hughes, Wolos et al. 1994), this treatment delayed the onset of CIA, with the index remaining low in these mice until day 37 (FIG. 14).

In the present study, treatment with methotrexate, a DMARD commonly used for the treatment of severe rheumatoid arthritis in humans (Hildner, Finotto et al. 1999), and known to be effective in delaying CIA in DBA/1- mice (Neurath, Hildner et al. 1999), was also effective in delaying CIA in the FcγRIIa transgenic mice (FIG. 14). Methotrexate was used at a low dose for 14 days from the time of the second collagen injection (1 mg/kg, ie 30 g/30 gm mouse from day 21-35) (FIG. 14). In both anti-CD3 and methotrexate treatment, arthritis was delayed due to depletion of inflammatory effector cells and disease increased in severity as immune function returned to normal after treatment ceased.

In contrast, treatment with anti-FcR agents (see above, examples 8 and 9) permanently halted disease progression, implying that essential initial steps in the inflammatory process were inhibited allowing disease prevention rather than delay. The data shown in FIG. 14 demonstrates that known treatments, including biological agents such as monoclonal antibodies and drugs such as methotrexate, effective for CIA in DBA/1 mice, are equally effective in the FcγRIIa transgenic mice. CIA in the DBA/1 mice has been used as a test model for anti-arthritis drugs for many years (Phadke, Fouts et al. 1985; Imaizumi, Hinoue et al. 1991). The data of the present study demonstrates that the FcγRIIa transgenic mice also respond to treatments that are effective in DBA/1 mice and these mice can therefore be used to test anti-arthritis drugs.

It will be appreciated by persons skilled in the art that numerous variations and/or modifications may be made to the invention as shown in the specific embodiments without departing from the spirit or scope of the invention as broadly described. The present embodiments are, therefore, to be considered in all respects as illustrative and not restrictive.

All publications discussed above are incorporated herein in their entirety. Any discussion of documents, acts, materials, devices, articles or the like which has been included in the present specification is solely for the purpose of providing a context for the present invention. It is not to be taken as an admission that any or all of these matters form part of the prior art base or were common general knowledge in the field relevant to the present invention as it existed in Australia or elsewhere before the priority date of each claim of this application.

REFERENCES:

Campbell, I. K., A. Bendele, et al. (1997). "Granulocyte-macrophage colony stimulating factor exacerbates collagen induced arthritis in mice." Ann Rheum Dis 56(6): 364-8.

Chuang, F., Saroli, M. and Unkeless, J. (2000). "Convergence of Fc gamma receptor IIA and Fc gamma receptor IIB signalling pathways in human neutrophils." J. Immunol. 164(1): 350-60.

Clynes, R., C. Dumitru, et al. (1998). "Uncoupling of immune complex formation and kidney damage in autoimmune glomerulonephritis." Science 279(5353): 10524.

Cosgrove, L. (1987). Monoclonal antibodies to platelet antigens. Department of Pathology. Melbourne, University of Melbourne.

Edworthy, S. (2001). Clinical manifestations of Systemic Lupus Erythematosus. Kelley's Textbook of Rheumatology. S. Ruddy, E. Harris and B. Sledge. Philadelphia, Pa., W. B. Saunders Company. 2:1105-1123.

Hildner, K., S. Finotto, et al. (1999). "Tumour necrosis factor (TNF) production by T cell receptor-primed T lymphocytes is a target for low dose methotrexate in rheumatoid arthritis." Clin Exp Immunol 118(1): 137-46.

Hughes, C., J. A. Wolos, et al. (1994). "Induction of T helper cell hyporesponsiveness in an experimental model of autoimmunity by using nonmitogenic anti-CD3 monoclonal antibody." J Immunol 153(7): 3319-25.

Imaizumi, K., H. Hinoue, et al. (1991). "Pathological evaluation of anti-rheumatic drugs on type II collagen-induced arthritis in DBA/1J mouse." Jikken Dobutsu 40(1): 95-9.

McKenzie, S. E., S. M. Taylor, et al. (1999). "The role of the human Fc receptor Fc gamma RIIA in the immune clearance of platelets: a transgenic mouse model." J Immunol 162(7): 4311-8.

Mottram, P. L., L. J. Murray-Segal, et al. (2002). "Remission and pancreas isograft survival in recent onset diabetic NOD mice after treatment with low-dose anti-CD3 monoclonal antibodies." Transpl Immunol 10(1): 63-72.

Neurath, M. F., K. Hildner, et al. (1999). "Methotrexate specifically modulates cytokine production by T cells and macrophages in murine collagen-induced arthritis (CIA): a mechanism for methotrexate-mediated immunosuppression." Clin Exp Immunol 115(1): 42-55.

Phadke, K., R. L. Fouts, et al. (1985). "Evaluation of the effects of various anti-arthritic drugs on type II collagen-induced mouse arthritis model." Immunopharmacology 10(1): 51-60.

The invention claimed is:

1. A method for screening a compound that is able to suppress aberrant immune activity, wherein the aberrant immune activity is selected from aberrant immune complex formation and immune complex induced inflammation, the method comprising the steps of:
   a. administering a compound to be screened to a transgenic mouse generated by transgenically modifying an embryo from a strain, derived from strains C57BL/6 and SJL, that is resistant to collagen-induced arthritis, such that said mouse comprises and expresses a transgene for human FcγRIIa receptor, whereby the expression of said FcγRIIa receptor renders the mouse susceptible to spontaneous development of an autoimmune disease selected from the group consisting of arthritis and systemic lupus erythematosus; and
   b. assessing the transgenic mouse to determine if the compound reduces said aberrant immune activity associated with arthritis or systemic lupus erythematosus in the mouse.

2. A method for screening a compound that is able to suppress an autoimmune disease caused by aberrant immune activity by suppressing aberrant immune activity selected from aberrant immune complex formation and immune complex induced inflammation, the method comprising the steps of:
   a. administering a compound to be screened to a transgenic mouse generated by transgenically modifying an embryo from a strain, derived from strains C57BL/6 and SJL, that is resistant to collagen-induced arthritis, such that said mouse comprises and expresses a transgene for human FcγRIIa receptor, whereby the expression of said FcγRIIa receptor renders the mouse susceptible to spontaneous development of an autoimmune disease selected from the group consisting of arthritis and systemic lupus erythematosus; and
   b. assessing the transgenic mouse to determine if the compound reduces said aberrant immune activity associated with arthritis or systemic lupus erythematosus in the mouse.

3. A method for screening a compound that is able to suppress an autoimmune disease caused by aberrant immune activity, the method comprising the steps of:
   a. administering a compound to be screened to a non-human cell expressing human FcγRIIa receptor, wherein the cell is selected from the group consisting of platelets, neutrophils, and macrophages, and wherein the cell is derived from a transgenic mouse generated by transgenically modifying an embryo from a strain, derived from strains C57BL/6 and SJL, that is resistant to collagen-induced arthritis, such that said mouse comprises and expresses a transgene for human FcγRIIa receptor, whereby the expression of said FcγRIIa receptor renders the mouse susceptible to spontaneous development of an autoimmune disease selected from the group consisting of arthritis and systemic lupus erythematosus; and
   b. assessing the cell to determine if the compound reduces said aberrant immune activity associated with arthritis or systemic lupus erythematosus in the cell.

4. A method according to claim 1, wherein the method comprises assessing the transgenic mouse to determine if the compound reduces immune complex induced inflammation.

5. A method according to claim 1, wherein the compound reduces aberrant immune activity in the transgenic mouse by inhibiting the activity of FcγRIIa expressed in the mouse.

6. A method according to claim 1, wherein in step (b) the aberrant immune activity is assessed in terms of clinical symptoms and/or pathological features of arthritis or systemic lupus erythematosus.

7. A method according to claim 1, wherein the autoimmune disease is rheumatoid arthritis (RA).

8. A method according to claim 1, wherein the autoimmune disease is collagen-induced arthritis (CIA).

9. A method according to claim 2, wherein the method comprises assessing the transgenic mouse to determine if the compound reduces immune complex induced inflammation.

10. A method according to claim 2, wherein the compound reduces aberrant immune activity in the transgenic mouse by inhibiting the activity of human FcγRIIa receptor expressed in the mouse.

11. A method according to claim 2, wherein in step (b) the aberrant immune activity is assessed in terms of clinical symptoms and/or pathological features of arthritis or systemic lupus erythematosus.

12. A method according to claim 2, wherein the autoimmune disease is rheumatoid arthritis (RA).

13. A method according to claim 2, wherein the autoimmune disease is collagen-induced arthritis (CIA).

14. A method according to claim 3, wherein the method comprises assessing the cell to determine if the compound reduces immune complex induced inflammation.

15. A method according to claim 3, wherein the compound reduces aberrant immune activity in the cell by inhibiting the activity of human FcγRIIa receptor expressed in the cell.

16. A method according to claim 3, wherein in step (b) the aberrant immune activity is assessed in terms of clinical symptoms and/or pathological features of arthritis or systemic lupus erythematosus.

17. A method according to claim 3, wherein the autoimmune disease is rheumatoid arthritis (RA).

18. A method according to claim 3, wherein the autoimmune disease is collagen-induced arthritis (CIA).

* * * * *